(12) United States Patent
Feder et al.

(10) Patent No.: US 7,374,765 B2
(45) Date of Patent: May 20, 2008

(54) METHODS AND COMPOSITIONS FOR DIAGNOSIS AND TREATMENT OF IRON MISREGULATION DISEASES

(75) Inventors: John N. Feder, San Carlos, CA (US); Randall C. Schatzman, Daly City, CA (US); Zenta Tsuchihashi, Menlo Park, CA (US)

(73) Assignee: Bio-Rad Laboratories, Inc., Hercules, CA (US)

(*) Notice: Subject to any disclaimer, the term of this patent is extended or adjusted under 35 U.S.C. 154(b) by 29 days.

(21) Appl. No.: 10/956,250

(22) Filed: Oct. 1, 2004

(65) Prior Publication Data

US 2005/0090430 A1    Apr. 28, 2005

Related U.S. Application Data

(60) Division of application No. 08/920,559, filed on Aug. 27, 1997, now Pat. No. 6,849,399, which is a continuation-in-part of application No. 08/652,265, filed on May 23, 1996, now Pat. No. 6,025,130, and a continuation-in-part of application No. 08/834,497, filed on Apr. 4, 1997, now Pat. No. 6,140,305, and a continuation-in-part of application No. 08/866,211, filed on Jun. 13, 1997, now abandoned.

(51) Int. Cl.
*A61K 39/395* (2006.01)
*A61K 39/00* (2006.01)
*A61K 39/38* (2006.01)
*A61K 45/00* (2006.01)
*A61K 47/00* (2006.01)

(52) U.S. Cl. ............... 424/185.1; 424/1.41; 424/1.57; 424/1.69; 424/130.1; 424/139.1; 424/143.1; 424/156.1; 424/184.1; 424/193.1; 424/278.1; 424/529; 435/325; 435/344; 436/63; 436/66; 530/388.22

(58) Field of Classification Search ............... 424/1.41, 424/1.57, 1.69, 184.1, 185.1, 193.1, 278.1, 424/529; 435/325, 344; 436/63, 66; 530/388.22
See application file for complete search history.

(56) References Cited

U.S. PATENT DOCUMENTS

| | | | |
|---|---|---|---|
| 4,399,216 A | 8/1983 | Axel et al. | |
| 4,434,156 A | 2/1984 | Trowbridge | |
| 4,511,503 A | 4/1985 | Olson et al. | |
| 4,666,927 A | 5/1987 | Hider et al. | |
| 4,683,202 A | 7/1987 | Mullis | |

(Continued)

FOREIGN PATENT DOCUMENTS

CA    2115221    8/1994

(Continued)

OTHER PUBLICATIONS

Harrison et al. 2003. J. of Hepatology. vol. 38:S14-S23.*

(Continued)

*Primary Examiner*—Mark Navarro
*Assistant Examiner*—J. Hines
(74) *Attorney, Agent, or Firm*—Jones Day

(57) ABSTRACT

Methods and compositions are provided for the diagnosis and treatment of iron misregulation diseases, including HFE polypeptides, agonists, and antagonists, and transferrin receptor agonists and antagonists.

1 Claim, 9 Drawing Sheets

U.S. PATENT DOCUMENTS

| | | | |
|---|---|---|---|
| 4,711,845 | A | 12/1987 | Gelfand et al. |
| 4,912,118 | A | 3/1990 | Hider et al. |
| 5,075,469 | A | 12/1991 | Chevion |
| 5,104,865 | A | 4/1992 | Hider et al. |
| 5,116,964 | A | 5/1992 | Capon et al. |
| 5,185,368 | A | 2/1993 | Peter et al. |
| 5,256,676 | A | 10/1993 | Hider et al. |
| 5,328,992 | A | 7/1994 | Peter et al. |
| 5,385,918 | A | 1/1995 | Connell et al. |
| 5,399,346 | A | 3/1995 | Anderson et al. |
| 5,420,008 | A | 5/1995 | Nishida et al. |
| 5,424,057 | A | 6/1995 | Peter et al. |
| 5,582,979 | A | 12/1996 | Weber |
| 5,705,343 | A | 1/1998 | Drayna et al. |
| 5,712,098 | A | 1/1998 | Tsuchihashi et al. |
| 5,719,125 | A | 2/1998 | Suzuki et al. |
| 5,753,438 | A | 5/1998 | Drayna et al. |
| 5,872,237 | A | 2/1999 | Feder et al. |
| 6,025,130 | A | 2/2000 | Thomas et al. |
| 6,140,305 | A | 10/2000 | Thomas et al. |
| 6,228,594 | B1 | 5/2001 | Thomas et al. |
| 6,284,732 | B1 | 9/2001 | Feder et al. |
| 6,391,852 | B1 | 5/2002 | Feder et al. |

FOREIGN PATENT DOCUMENTS

| | | |
|---|---|---|
| CA | 2115222 | 8/1994 |
| CA | 2115224 | 8/1994 |
| DE | 208 609 | 4/1984 |
| DE | 4 327 226 | 2/1995 |
| EP | 0 315 434 | 5/1989 |
| EP | 0 346 281 | 12/1989 |
| EP | 97910741 | 6/2003 |
| GB | 2 293 269 | 3/1996 |
| WO | WO 94/01463 | 1/1994 |
| WO | WO 94/04186 | 3/1994 |
| WO | WO 94/11367 | 5/1994 |
| WO | WO 94/21243 | 9/1994 |
| WO | WO 95/16663 | 6/1995 |
| WO | WO 96/06583 | 3/1996 |
| WO | WO 96/17870 | 6/1996 |
| WO | WO 96/35802 | 11/1996 |
| WO | WO 97/38137 | * 10/1997 |
| WO | WO 98/56814 | * 12/1998 |

OTHER PUBLICATIONS

Hemochromatosis-Genetics Home Reference. http://ghr.nlm.nih.giv/condition+hemochromatosis□□.*

Beutler, E. et al., "Mutation Analysis in Hereditary Hemochromatosis" *Blood Cells, Molecules, and Diseases* (1996), 22(16): 187-194.

Gasparini, et al, "Where does the gene for Hemochromatosis lie in relation to HLA-A", *Hepatology* (1994), 19: 1050-1056.

VogeL, et al., "Human Chromosomes," Springer-Verlag (1992) pp. 18-81.

Seese, et al., "Localization of the Hemochromatosis Disease Gene : Linkage Disequilibrium Analysis using an American Patient Collection," *Blood Cells, Molecules & Diseases* (1996) 22:36-46.

Gandon et al., "Linkage Disequilibrium and Extended Haplotypes in the HLA-A to D6S105 Region: Implications for Mapping the Hemochromatosis Gene (HFE),"*J. Hum. Genet.* (1996) 97(1):103-13.

Adams, M.D., et al., "*Complementary DNA Sequencing: Expressed Sequence Tags and Human Genome Project*," Science (1991) 252:1651-1656 (National Institutes of Health).

Amadou, C., et al., "*Localization of New Genes and Markers to the Distal Part of the Human Major Histocompatibility Complex (MHC) Region and Comparison With the Mouse: New Insights Into the Evolution of Mammalian Genomes*," Genomics (1995) 26:9-20.

Anderson, J.R., et al., "*Precipitating Autoantibodies in Sjögren's Disease*," Lancet (1961) 2:456-460 (Glasgow Univ.).

Bacon, B.R., "*Causes of Iron Overload*," N. Engl. J. Med. (1992) 326(2):126-127 (St. Louis Univ. School of Medicine).

Balan, V., et al., "*Screening for Hemochromatosis: A Cost-Effectiveness Study Based on 12,258 Patients*," Gastroenterology (1994) 107:453-459.

Barton, J.C., et al., "*Blood Lead Concentrations in Hereditary Hemochromatosis*," J. Lab. Clin. Med. (1994) 124(2):193-198.

Barton, J.C., et al., "*Hemochromatosis: The Genetic Disorder of the Twenty-First Century*," Nature Medicine (1996) 2(4):394-395 (Brookwood Medical Center).

Beaucage, S.L., et al., "*Deoxynucleoside Phosphoramidites-A New Class of Key Intermediates for Deoxypolynucleotide Synthesis*," Tetrahedron Letters (1981) 22(20):1859-1862.

Beggs, J.D., "*Transformation of Yeast by a Replicating Hybrid Plasmid*," Nature (1978) 275:104-109.

Benton, W.D., et al., "*Screening λgt Recombinant Clones by Hybridization to Single Plaques in situ*," Science (1977) 196:180-182 (National Institutes of Health).

Beutler, E., et al., "*A Strategy for Cloning the Hereditary Hemochromatosis Gene*," Blood Cells, Molecules, and Diseases (1995) 21(21):207-216.

Boretto, J., et al., "*Anonymous Markers Located on Chromosome 6 in the HLA-A Class I Region: Allelic Distribution in Genetic Haemochromatosis*," Hum. Genet. (1992) 89:33-36 (Institut National de la Santa et de la Recherche Medicale).

Botstein, D., et al., "*Sterile Host Yeasts (SHY): A Eukaryotic System of Biological Containment for Recombinant DNA Experiments*," Gene (1979) 8:17-24 (American Cancer Society).

Broach, J.R., et al., "*Transformation in Yeast: Development of a Hybrid Cloning Vector and Isolation of the CAN1 Gene*," Gene (1979) 8:121-133 (National Institutes of Health).

Calandro, L.M., et al., "*Characterization of a Recombinant That Locates the Hereditary Hemochromatosis Gene Telomeric to HLA-F*," Hum. Genet. (1995) 96:339-342 (Kaiser Foundation Research Institute).

Camaschella, C., et al., "*Hereditary Hemochromatosis: Recent Advances in Molecular Genetics and Clinical Management*," Haematologica (1997) 82:77-84 (BioMed).

Campbell, A.M., "*Monoclonal Antibody Technology*," Elsevier Science Publishers (1985) Chapter 1 pp. 1-32 (ISBN 0-444-80592-3).

Capecchi, M.R., "*Altering the Genome by Homologous Recombination*," Science (1989) 244:1288-1292 (Univ. of Utah Medical Center).

Cartwright, G.E., et al., "*Inheritance of Hemochromatosis: Linkage to HLA*," Trans. Assoc. Am. Phys. (1978) 91:273-281 (National Institutes of Health).

Chen, X., et al., "*Template-Directed Dye-Terminator Incorporation (TDI) Assay: A Homogeneous DNA Diagnostic Method Based on Fluorescence Resonance Energy Transfer*," Nucl. Acids Res. (1997) 25(2):347-353 (U.S. Dept. of Energy).

Chong, S.S., et al., "*Molecular Cloning of the cDNA Encoding a Human Renal Sodium Phosphate Transport Protein and its Assignment to Chromosome 6p21.3-p23*," Genomics (1993) 18:355-359.

Church, D.M., et al., "*Isolation of Genes From Complex Sources of Mammalian Genomic DNA Using Exon Amplificaiton*," Nature Genetics (1994) 6:98-105 (National Institutes of Health).

Clark, G., et al., "*Characterization of a Soluble Cytoplasmic Antigen Reactive With Sera From Patients With Systemic Lupus Erythmatosus*," J. Immunol. (1969) 102(1):117-122 (Univ. of New York Dept. of Medicine).

Cornall, R.J., et al., "The Generation of a Library of PCR-Analyzed Microsatellite Variants for Genetic Mapping of the Mouse Genome," Genomics (1991) 10:874-881.

Crawford, D.H.G., et al., "*Evidence That the Ancestral Haplotype in Australian Hemochromatosis Patients May be Associated With a Common Mutation in the Gene*," Am. J. Hum. Genet. (1995) 57:362-367.

Crystal, R.G., "*Gene Therapy Strategies for Pulmonary Disease*," Am. J. Med. (1992) 92(6A):6A-44S-6A-52S (National Institutes of Health).

Darnell, J., "*Tools of Molecular Cell Biology: Molecular Technology*," Scientific American Books (1986) pp. 227-229 (Rockefeller Univ.).

Dausset, J., et al., "*Centre d'Etude du Polymorphisme Humain (CEPH): Collaborative Genetic Mapping of the Human Genome,*" Genomics (1990) 6:575-577.

de Sousa, M., et al., "*Iron Overload in $\beta_2$-Microglobulin-Deficient Mice,*" Immun. Lett. (1994) 39:105-111.

Dugast, I.J., et al., "*Identification of Two Human Ferritin H Genes on the Short Arm of Chromosome 6,*" Genomics (1990) 6:204-211.

Edwards, C.Q., et al., "*The Locus for Hereditary Hemochromatosis Maps Between HLA-A and HLA-B,*" Cytogenet. Cell Genet. (1985) 40:620 (Univ. of Utah Medical Center).

Edwards, C.Q., et al., "*Screening for Hemochromatosis,*" New Engl. J. Med. (1993) 328(22):1616-1619 (Univ. of Utah College of Medicine).

El Kahloun, A., et al., "*Localization of Seven New Genes Around the HLA-A Locus,*" Hum. Molec. Genet. (1992) 2(1):55-60 (Institut National de la Sante et de la Recherche Medicale).

Fahy, E., et al., "*Self-Sustained Sequence Replication (3SR): An Isothermal Transcription-Based Amplification System Alternative to PCR,*" PRC Methods and Applications (1991) 1:25-33.

Finch, C.A., "*Hemochromatosi—Treatment is Easy, Diagnosis Hard,*" Western J. Med (1990 153(3):323-325 (Univ. of Washington School of Medicine).

Freemont, P.S., et al., "*A Novel Cysteine-Rich Sequence Motif,*" Cell (1991) 65:483-484 (Imperial Cancer Research Fund).

Friedmann, T., "*Progress Toward Human Gene Therapy,*" Science (1989) 244:1275-1281 (San Diego Univ. of Calif.).

Fullan, A., et al., "*A Polymorphic Dinucleotide Repeat at the Human HLA-F Locus,*" Hum. Mol. Genet. (1994) 3(12):2266 (Mercator Genetics).

Gasparini, P., et al., "*Linkage Analysis of 6p21 Polymorphic Markers and the Hereditary Hemochromatosis: Localization of the Gene Centromeric to HLA-F,*" Hum. Molec. Genet. (1993) 2(5):571-576 (National Research Council).

Gnirke, A., et al., "*Physical Calibration of Yeast Aritficial Chromosome Contig Maps by RecA-Assisted Restriction Endonuclease (RARE) Cleavage,*" Genomics (1994) 24:199-210.

Goei, V.L., et al., "*Isolation of Novel Non-HLA Gene Fragments From the Hemochromatosis Region (6p21.3) by cDNA Hybridization Selection,*" Am. J. Hum. Genet. (1994) 54:244-251.

Gorski, J., "*HLA-DR $\beta$-Chain Polymorphism: Second Domain Polymorphism Reflects Evolutionary Relatedness of Alleles and May Explain Public Serologic Epitiopes,*" J. Immunol. (1989) 143(1):329-333.

Gruen, J.R., et al., "*Physical and Genetic Mapping of the Telomeric Major Histocompatibility Complex Region in Man and Relevance to the Primary Hemochromatosis Gene (HFE),*" Genomics (1992) 14:232-240.

Grunstein, M., et al., "*Colony Hybridization: A Method for the Isolation of Cloned DNAs That Contain a Specific Gene,*" Proc. Natl. Acad. Sci. USA (1975) 72(10):3961-3965 (National Science Foundation).

Gubler, U., et al., "*A Simple and Very Efficient Method for Generating cDNA Libraries,*" Gene (1983) 25:263-269.

Gyapay, G., et al., "*The 1993-1994 Genethon Human Genetic Linkage Map,*" Nature Genetics (1994) 7:246-339 (Assoc. Francais conte les Myopathies).

Halliday, J.W., "*Hemochromatosis and Iron Needs,*" Nutr. Rev. (1998) 56(2):S30-S37 (Queensland Institute of Medical Research).

Harlow, E., et al., "*Antibodies: A Laboratory Manual,*" Cold Spring Harbor Laboratory (1988) Chapter 5 pp. 75-81 (ISBN 0-87969-314-2).

Hashimoto, K., et al., "*Identification of a Mouse Homolog for the Human Hereditary Haemochromatosis Candidate Gene,*" Biochem. Biophys. Res. Comm. (1997) 230:35-39.

Herskowitz, I., et al., "*The Lysis-Lysogeny Decision of Phage $\lambda$: Explicit Programming and Responsiveness,*" Ann. Rev. Genet. (1980) 14:399-445.

Hinnen, A., et al., "*Tranformation of Yeast,*" Proc. Natl. Acad. Sci. USA (1978) 75(4):1929-1933 (National Science Foundation).

Ito, H., et al., "*Transformation of Intact Yeast Cells Treated With Alkali Cations,*" J. Bacteriol. (1983) 153(1):163-168.

Jack, L.J.W., et al., "*Cloning and Analysis of cDNA Encoding Bovine Butyrophilin, an Apical Glycoprotein Expressed in Mammary Tissue and Secreted in Association With the Milk-fat Globule Membrane During Lactation,*" J. Biol. Chem. (1990) 265(24):14481-14486 (National Science Foundation).

Jakobovits, A., et al., "*Production of Antigen-Specific Human Antibodies from Mice Engineered with Human Heavy and Light Chain YACs$^a$*", Ann. N.Y. Acad. Sci. (1995) 764:525-535 (Cell Genesys, Inc.).

Jazwinska, E.C., et al., "*Localization of the Hemochromatosis Gene Close to D6S105,*" Am. J. Hum. Genet. (1993) 53:347-352.

Jazwinska, E.C., et al., "*Haplotype Analysis in Australian Hemochromatosis Patients: Evidence for a Predominant Ancestral Haplotype Exclusively Associated with Hemochromatosis,*" Am. J. Hum. Genet. (1995) 56:428-433.

Jazwinska, E.C., et al., "*Where Does the Gene for Hemochromatosis Lie in Relation to HLA-A?,*" Hepatology (1994) 19:1050-1051 (Queensland Institute of Medical Research).

Jazwinska, E.C., et al., "*Hemochromatosis and "HLA-H": Definite!,*" Hepatology (1997) 25(2):495-496 (Queensland Institute of Medical Research).

Jouet, M.M.H., et al., "*Isolation of YAC Clones Containing Class I HLA Genes Which Map in the Vicinity of the Hereditary Haemochromatosis Gene,*" J. Med. Genet. (1991) 28(8):572 (St. Mary's Hospital, Manchester).

Koller, B.H., et al., "*Normal Development of Mice Deficient in $\beta_2M$, MHC Class I Proteins, and CD8$^+$ T Cells,*" Science (1990) 248:1227-1230 (National Institutes of Health).

Kramer, M.F., et al., "*The Polymerase Chain Reaction,*" Current Protocols in Molecular Biology (1993) Chapter 15 pp. 15.0.1-15.1.14 (ISBN 0-471-30661-4).

Lemarchand, P., et al., "*Adenovirus-Mediated Transfer of a Recombinant Human $\alpha_1$-Antitrypsin cDNA to Human Endothelial Cells,*" Proc. Natl. Acad. Sci. USA (1992) 89:6482-6486 (National Institutes of Health).

Levy-Lahad, E., et al., "*Candidate Gene for the Chromosome I Familial Alzheimer's Disease Locus,*" Science (1995) 269:973-977 (National Institute on Aging for the Alzheimer's Diseases Research Center).

Lipinski, M., et al., "*Idiopathic Hemochromatosis: Linkage with HLA,*" Tissue Antigens (1978) 11:471-474 (Hopital Saint-Louis, Paris).

Lovett, M., et al., "*Direct Selection: A Method for the Isolation of cDNAs Encoded by Large Genomic Regions,*" Proc. Natl. Acad. Sci. USA (1991) 88:9628-9632 (National Center for Human Genome Research).

Maskos, U., et al., "*A Novel Method for the Parallel Analysis of Multiple Mutations in Multiple Samples,*" Nucl. Acids Res. (1993) 21(9):2269-2270 (Univ. of Oxford).

Matteucci, M.D., et al., "*Synthesis of Deoxyoligonucleotides on a Polymer Support,*" J. Am. Chem. Soc. (1981) 103:3185-3191 (National Institutes of Health).

Maxam, A.M., et al., "*Sequencing End-Labeled DNA With Base-Specific Chemical Cleavages,*" Methods in Enzymology (1980) 65:499-560 (ISBN 0-12-181965-5).

Miller, M.M., et al., "*Immunoglobulin Variable-Region-Like Domains of Diverse Sequence Within the Major Histocompatibility Complex of the Chicken,*" Proc. Natl. Acad. Sci. USA (1991) 88:4377-4381 (National Institutes of Health).

Miyazaki, J.I., et al., "*Intracellular Transport Blockade Caused by Disruption of the Disulfide Bridge in the Third External Domain of Major Histocompatibility Complex Class I Antigen,*" Proc. Natl. Acad. Sci. USA (1986) 83:757-761 (National Institutes of Health).

Morgan, J.G., et al., "*The Selective Isolation of Novel cDNAs Encoded by the Regions Surrounding the Human Interleukin 4 and 5 Genes,* " Nucl. Acids Res. (1992) 20(19):5173-5179 (National Center for Human Genome Research).

Murray, J.C., et al., "*A Comprehensive Human Linkage Map with Centimorgan Density,*" Science (1994) 265:2049-2054 (Univ. of Iowa).

Needham-VanDevanter, D.R., et al., "*Characterization of an Adduct Between CC-1065 and a Defined Oligodeoxynucleotide Duplex,*" Nucl. Acids Res. (1984) 12(15):6159-6168 (Welch Foundation).

Needleman, S.B., et al., "*A General Method Applicable to the Search for Similarities in the Amino Acid Sequence of Two Proteins,*" J. Mol. Biol. (1970) 48:443-453 (U.S. Public Health Service).

Nickerson, D.A., et al., "*Automated DNA Diagnostics Using an ELISA-Based Oligonucleotide Ligation Assay,*" Proc. Natl. Acad. Sci. USA (1990) 87:8923-8927 (Whittier Foundation).

Nickerson, D.A., et al., "*Genotyping by Ligation Assays,*" Current Protocols in Human Genetics (1994) Chapter 2.6 pp. 2.6.1-2.6.4 (ISBN 0-471-03420-7).

Nierman, W.C., et al., "*ATCC/NIH Repository Catalogue of Human and Mouse DNA Probes and Libraries,*" Amer. Type Culture Coll. (1994) pp. 1-70 (ISBN 0-930009-56-8).

Olynyk, J.K., et al., "*Hepatic Iron Concentration as a Predictor of Response to Interferon Alfa Therapy in Chronic Hepatitis C,*" Gastroenterology (1995) 108:1104-1109.

Orphanos, V., et al., "*Thirteen Dinucleotide Repeat Polymorphisms on Chromosome 6,*" Hum. Mol. Genet. (1993) 2(12):2196 (Cancer Genetics).

Wettstein, D.A., et al., "*Expression of a Class II Major Histocompatibility Complex (MHC) Heterodimer in a Lipid-Linked Form With Enhanced Peptide/Soluble MHC Complex Formation at Low pH,*" J. Exp. Med. (1991) 174:219-228.

Worwood, M., et al., "*Alleles at D6S265 and D6S105 Define a Haemochromatosis-Specific Genotype,*" Brit. J. Hematol. (1994) 86:863-866 (Univ. of Wales College of Medicine).

Wu, D.Y., et al., "*The Ligation Amplification Reaction (LAR)-Amplification of Specific DNA Sequences Using Sequential Rounds of Template-Dependent Ligation,*" Genomics (1989) 4:560-569.

Yanofsky, C., et al., "*Repression is Relieved Before Attenuation in the trp Operon of Escherichia coli as Tryptophan Starvation Becomes Increasingly Severe,*" J. Bacter. (1994) 158(3):1018-1024.

Youil, R., et al., "*Screeening for Mutations by Enzyme Mismatch Cleavage With T4 Endonuclease VII,*" Proc. Natl. Acad. Sci. USA (1995) 92:87-91 (National Health and Medical Research Council of Australia).

Yu, C-E., et al., "*Positional Cloning of the Werner's Syndrome Gene,*" Science (1996) 272:258-262 (National Institute on Aging).

Zijlstra, M., et al., "*$\beta$2-Microglobulin Deficient Mice Lack CD4$^-$8$^+$ Cytolytic T Cells,*" Nature (1990) 344:742-746 (Cancer Research Institute).

Zinkernagel, R.M., et al., "*MHC-Restricted Cytotoxic T Cells: Studies on the Biological Role of Polymorphic Major Transplantation Antigens Determining T-Cell Restriction-Specificity, Function, and Responsiveness,*" Adv. In Immunol. (1979) 2751-177 (ISBN 0-12-022427-5).

\* cited by examiner

Figure 4.  The nucleotide sequence of the HFE cDNA (cDNA 24)

```
ccacgcgtccggggggacactggatcacctagtgtttcacaagcaggtaccttctgctgt
aggagagagagaactaaagttctgaaagacctgttgcttttcaccaggaagtttactgg
gcatctcctgagcctaggcaatagctgtagggtgacttctggagccatcccgtttcccc
gcccccaaaagaagcggagatttaacggggacgtgcggccagagctggggaaatgggcc
cgcgagccaggccggcgcttctcctcctgatgcttttgcagaccgcggtcctgcaggggc
gcttgctgcgttcacactctctgcactacctcttcatgggtgcctcagagcaggaccttg
gtctttccttgtttgaagctttgggctacgtggatgaccagctgttcgtgttctatgatc
atgagagtcgccgtgtggagccccgaactccatgggtttccagtagaatttcaagccaga
tgtggctgcagctgagtcagagtctgaaagggtgggatcacatgttcactgttgacttct
ggactattatggaaaatcacaaccacagcaaggagtcccacaccctgcaggtcatcctgg
gctgtgaaatgcaagaagacaacagtaccgagggctactggaagtacgggtatgatgggc
aggaccaccttgaattctgccctgacacactggattggagagcagcagaacccagggcct
ggcccaccaagctggagtgggaaaggcacaagattcgggccaggcagaacagggcctacc
tggagagggactgccctgcacagctgcagcagttgctggagctggggagaggtgttttgg
accaacaagtgcctcctttggtgaaggtgacacatcatgtgacctcttcagtgaccactc
tacggtgtcgggccttgaactactaccccagaacatcaccatgaagtggctgaaggata
agcagccaatggatgccaaggagttcgaacctaaagacgtattgcccaatggggatggga
cctaccagggctggataaccttggctgtaccccctggggaagagcagagatatacgtgcc
aggtggagcacccaggcctggatcagcccctcattgtgatctgggagccctcaccgtctg
gcaccctagtcattggagtcatcagtggaattgctgttttttgtcgtcatcttgttcattg
gaatttgttcataatattaaggaagaggcagggttcaagaggagccatggggcactacg
tcttagctgaacgtgagtgacacgcagcctgcagactcactgtgggaaggagacaaaact
agagactcaaagagggagtgcatttatgagctcttcatgtttcaggagagagttgaacct
aaacatagaaattgcctgacgaactccttgatttagccttctctgttcatttcctcaaa
aagatttcccatttaggtttctgagttcctgcatgccggtgatccctagctgtgacctc
tcccctggaactgtctctcatgaacctcaagctgcatctagaggcttccttcatttcctc
cgtcacctcagagacatacacctatgtcatttcatttcctattttggaagaggactcct
taaatttgggggacttacatgattcattttaacatctgagaaaagctttgaaccctggga
cgtggctagtcataaccttaccagattttacacatgtatctatgcattttctggacccg
ttcaacttttcctttgaatcctctctctgtgttacccagtaactcatctgtcaccaagcc
ttggggattcttccatctgattgtgatgtgagttgcacagctatgaaggctgtgcactgc
acgaatggaagaggcacctgtcccagaaaaagcatcatggctatctgtgggtagtatgat
gggtgttttagcaggtaggaggcaaatatcttgaaaggggttgtgaagaggtgttttt
ctaattggcatgaaggtgtcatacagatttgcaaagtttaatggtgccttcatttgggat
gctactctagtattccagacctgaagaatcacaataatttctacctggtctctccttgt
tctgataatgaaaattatgataaggatgataaaagcacttacttcgtgtccgactcttct
gagcacctacttacatgcattactgcatgcacttcttacaataattctatgagataggta
ctattatccccatttcttttttaaatgaagaaagtgaagtaggccgggcacggtggctcg
cgcctgtggtcccagggtgctgagattgcaggtgtgagccaccctgcccagccgtcaaaa
gagtcttaatatatatatccagatggcatgtgtttactttatgttactacatgcacttgg
ctgcataaatgtggtacaaccattctgtcttgaagggcaggtgcttcaggataccatata
cagctcagaagtttcttctttaggcattaaattttagcaaagatatctcatctcttctt
taaaccatttctttttttgtggttagaaaagttatgtagaaaaaagtaaatgtgattta
cgctcattgtagaaaagctataaaatgaatacaattaaagctgttatttaattagccagt
gaaaaactattaacaacttgtctattacctgttagtattattgttgcattaaaaatgcat
atactttaataaatgtacattgtattgtaaaaaaaaaaa
```

Figure 5 .Primary structure of the HFE protein

MGPRARPALLLLMLLQTAVLQG                          Leader
                                                sequence RLLRSHSLHYLFMGASEQDLGLSLFEALGYVDDQLFVFYDHeSRRVEPRTPWVSSRISSQ
MWLQLSQSLKGWDHMFTVDFWTIMENHNHSKE                alpha 1 domain SHTLQVILGCEMQEDNSTEGYWKYGYDGQDHLEFCPDTLDWRAAEPRAWPTKLEWERHKIR
ARQNRAYLERDCPAQLQQLLELGRGVLDQQ                  alpha 2 domain VPPLVKVTHHVTSSVTTLRCRALNYYPQNITMKWLKDKQPMDAKEFEPKDVLPNGDGTYQG
WITLAVPPGEEQRYTCQVEHPGLDQPLIVIW                alpha 3 domain EPSPSGTLVIGVISGIAVFVVILFIGILFIIL                transmembrane
                                                domain

RKRQGSRGAMGHYVLAERE                             cytoplasmic
                                                domain

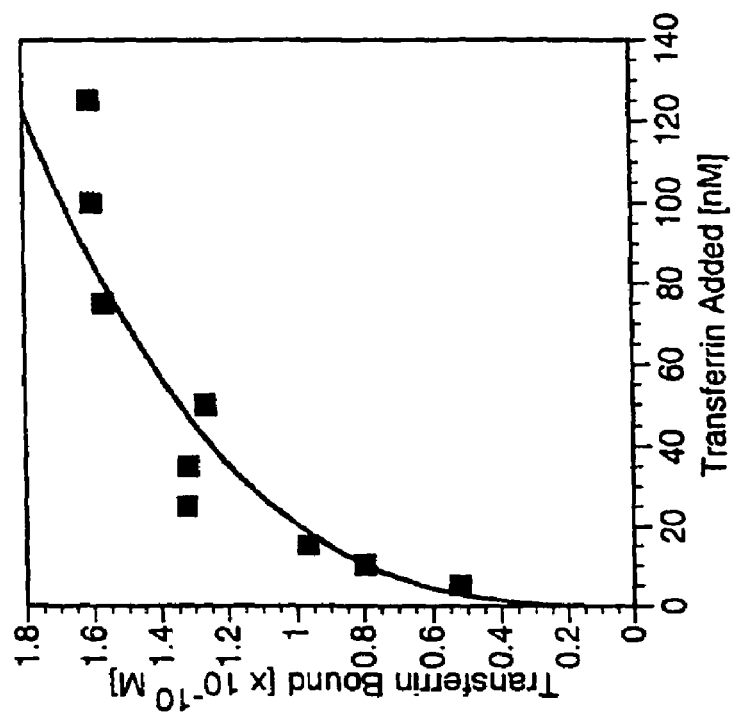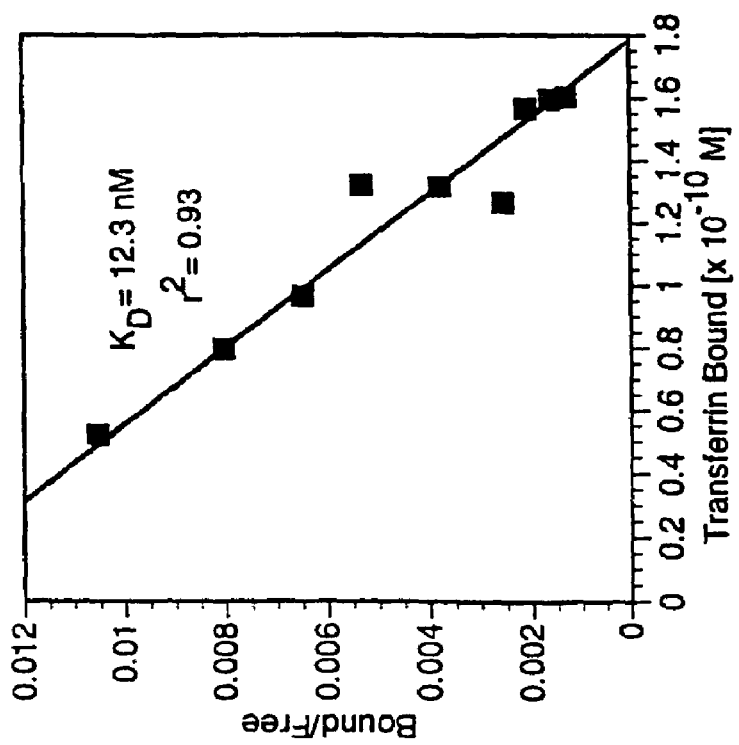
FIG. 6

METHODS AND COMPOSITIONS FOR DIAGNOSIS AND TREATMENT OF IRON MISREGULATION DISEASES

This application is a divisional of U.S. Ser. No. 08/920,559, filed Aug. 27, 1997 now U.S. Pat. No. 6,849,399, which is a continuation-in-part of U.S. Ser. No. 08/652,265, filed May 23, 1996, now U.S. Pat. No. 6,025,130, U.S. Ser. No. 08/834,497, filed Apr. 4, 1997, now U.S. Pat. No. 6,140,305, and U.S. Ser. No. 08/866,211, filed Jun. 13, 1997, now abandoned, the disclosures of which are incorporated herein in their entirety for all purposes.

BACKGROUND OF THE INVENTION

Hereditary hemochromatosis (HH), is a common disease characterized by excess iron deposition in the major organs of the body (Dadone, M. M. et al. *AM. J. Clin. Pathol.* 78:196-207 (1982); Edwards, C. Q. et al. *N. Engl. J. Med.* 18:1355-1362. (1988); McLaren, C. E., et al. *Blood* 86:2021-2027 (1995); Bothwell, T. H. et al., *The metabolic and molecular basis of inherited disease* (ed. C. R. Scriver, E. A.) 2237-2269 (McGraw-Hill, New York, 1995); Bacon, B. R. et al. *Hepatoloy. A textbook of liver disease* (eds. Zakim, D. & Boyer, T. D.) 1439-1472 (W. B. Saunders, Philadelphia, 1996). A candidate gene for this disease, HFE, was identified by positional cloning (Feder, J. N., et al. *Nature Genetics* 13:399-408 (1996)). The gene, a novel member of the MHC class I family, was found to have a mutation, Cys282Tyr, in 83% of patient chromosomes (Feder, J. N., et al. *Nature Genetics* 13:399-408 (1996)). This mutation eliminates the ability of HFE to associate with $\beta_2$-microglobulin ($\beta_2$m) and prevents cell-surface expression (Feder, J. N., et al., *J. Biol. Chem.* 272:14025-14028 (1997)). However, the relationship of this class I-like molecule to the regulation of iron metabolism has remained obscure.

Thus, an object of the instant invention is to provide a molecular basis for the relationship of HFE to iron metabolism, and diagnostic and therapeutic agents for the treatment of iron misregulation diseases.

SUMMARY OF THE INVENTION

One aspect of the invention is a method of treating an iron overload disease in a patient comprising administering to a patient a therapeutically effective amount of an HFE polypeptide.

A further aspect of the invention is a method of diagnosing an iron misregulation disease in a patient comprising assaying binding of a ligand from the patient to a transferrin receptor.

A further aspect of the invention is a method of treating an iron overload disease in a patient comprising administering to the patient an antagonist of the transferrin receptor.

A further aspect of the invention is a method for diagnosing an iron misregulation disease in a patient comprising detecting a mutation in a transferrin receptor gene in a nucleic acid sample from the patient.

A further aspect of the invention is a method of treating an iron deficiency disease in a patient comprising administering to the patient a transferrin receptor agonist.

A further aspect of the invention is a method of treating an iron deficiency disease in a patient comprising administering to the patient an antagonist of HFE.

A further aspect of the invention is a method of treating an iron overload disease in a patient comprising administering to the patient an agonist of HFE.

A further aspect of the invention is a method of inhibiting tumor cell growth comprising contacting a tumor cell with an HFE polypeptide.

A further aspect of the invention is a method of diagnosing an iron misregulation disease in a patient comprising assaying binding of a ligand to a transferrin receptor isolated from the patient.

A further aspect of the invention is a method of diagnosing an iron misregulation disease in a patient comprising detecting a mutation in a transferrin gene in a nucleic acid sample from the patient.

BRIEF DESCRIPTION OF THE FIGURES

(FIG. 1A) HFE antibodies immunoprecipitate 12, 49, 100, and 200 kDa surface-labeled proteins from wild-type HFE expressing cells but not from parental 293 (human embryonic kidney cells, ATCC CRL 1573) or Cys282Tyr HFE mutant expressing cells. (FIG. 1B) FLAG epitope antibodies also immunoprecipitate 12, 49, 100, and 200 kDa surface-labeled proteins in wild-type HFE expressing cells but not parental 293 or Cys282Tyr HFE mutant expressing cells. (FIG. 1C) TfR antibodies immunoprecipitate 100 and 200 kDa surface-labeled proteins from parental 293, wild-type and Cys282Tyr HFE expressing cells and in addition, detect $\beta_2$m (12 kDa) and HFE (49 kDa) proteins only in wild-type HFE expressing cells. (FIG. 1D) HLA-ABC antibodies fail to immunoprecipitate 100 and 200 kDa proteins from parental 293 cells.

(FIG. 2A) HFE antibodies co-immunoprecipitate TfR from wild-type and His63Asp HFE expressing cells but not 293 or Cys282Tyr HFE mutant expressing cells. (FIG. 2B) HFE antibodies immunoprecipitate similar amounts of HFE protein from wild-type, Cys282Tyr and His63Asp HFE expressing cells. (FIG. 2C) TfR antibodies co-immunoprecipitate HFE from wild-type and His63Asp HFE expressor cells but not parental 293 or Cys282Tyr mutant expressing cells. (FIG. 2D) TfR antibodies immunoprecipitate similar amounts of TfR protein from parental 293, and wild-type, Cys282Tyr and His63Asp HFE expressing cells. (FIG. 2E) FLAG epitope (M2) antibodies co-immunoprecipitate TfR from wild-type and His63Asp HFE expressing cells but not parental 293 or Cys282Tyr HFE mutant expressing cells.

FIG. 3 (A-C). Effect of HFE on $^{125}$I-transferrin binding to the TfR.

FIG. 4 depicts the nucleotide sequence of the HFE cDNA (SEQ ID NO:1).

FIG. 5 depicts the amino acid sequence of the HFE protein (SEQ ID NO:2-7).

FIGS. 6A and B depict the effect of His63Asp mutant HFE protein on [$^{125}$I]-transferrin binding. (Panel A) Scatchard analysis revealed an apparent $K_D$ of approximately 12 nM, with an apparent number of binding sites of 2×10⁵ sites/cell. (Panel B) Transferrin binding to TfR in cells overexpressing the His63Asp mutant HFE protein.

SPECIFIC EMBODIMENTS OF THE INVENTION

Figure 1:
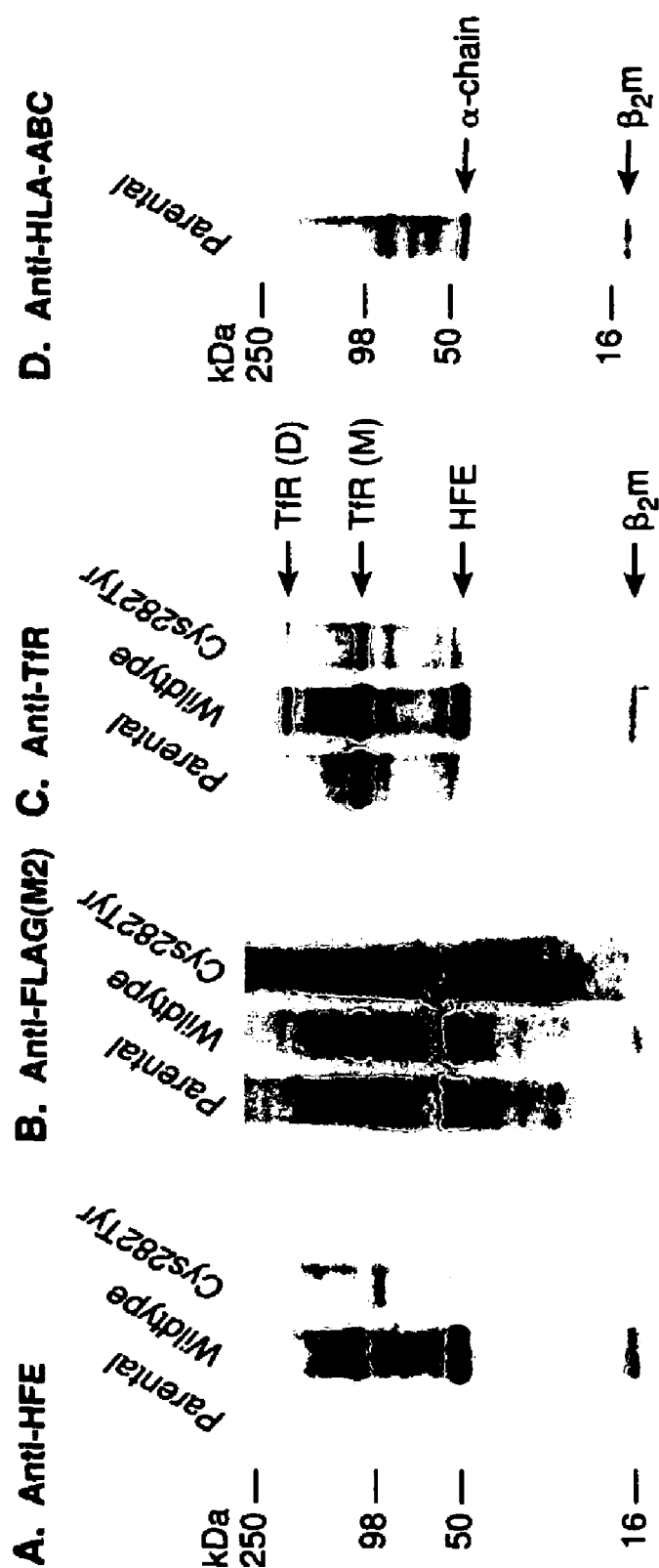
FIG. 1 (A-D). Cell-surface labeling of HFE (expressed as a FLAG epitope fusion) and association with TfR.

The term "iron misregulation diseases" as used herein is intended to include both iron overload diseases and iron deficiency diseases.

The term "iron overload diseases" as defined herein is intended to include primary or secondary iron overload diseases, syndromes, or conditions such as, but not limited to, porphyria cutanea tarda, hereditary spherocytosis, hyprochromic anemia, dysererythropoietic anemia (CDAI), faciogenital dysplasia (FGDY), Aarskog syndrome, atransferrinemia, sideroblastic anemia (SA), hereditary hemochromatosis (HH), pyridoxine-responsive sidero-blastic anemia, and hemoglobinopathies such as thalassemia and sickle cell.

The term "iron deficiency diseases" as used herein is intended to include diseases, syndromes, or conditions resulting in an iron deficiency in a patient, including but not limited to iron deficiencies resulting from pregnancy, cancer, beeturia, gastrectomy, achlorhydria, iron deficient anemias, chronic anemias, chronic diarrhea, nontropical sprue, idiopathic pulmonary hemosiderosis, and von Willebrand's disease. The term additionally includes but is not limited to microbially induced iron depletion, such as from *Malaria falciparum*, and iron deficiency resulting from blood loss due to injury, parasitic infection such as hookworm, menstruation, and hereditary telangiectasia.

The term "vector" as used herein refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome. A vector contains multiple genetic elements positionally and sequentially oriented, i.e., operatively linked with other necessary elements such that nucleic acid in the vector encoding an HFE polypeptide can be transcribed, and when necessary, translated in transfected cells.

The term "gene" as used herein is intended to refer to a nucleic acid sequence which encodes a polypeptide. This definition includes various sequence polymorphisms, mutations, and/or sequence variants wherein such alterations do not affect the function of the gene product. The term "gene" is intended to include not only coding sequences but also regulatory regions such as promoters, enhancers, and termination regions. The term further includes all introns and other DNA sequences spliced from the mRNA transcript, along with variants resulting from alternative splice sites.

The term "plasmid" refers to an autonomous circular DNA molecule capable of replication in a cell, and includes both the expression and nonexpression types. Where a recombinant microorganism or cell culture is described as hosting an "expression plasmid", this includes both extrachromosomal circular DNA molecules and DNA that has been incorporated into the host chromosome(s). Where a plasmid is being maintained by a host cell, the plasmid is either being stably replicated by the cells during mitosis as an autonomous structure or is incorporated within the host's genome.

In some embodiments of the invention, HFE polypeptides are provided for therapeutic use in patients having symptoms of a primary iron overload disease or syndrome, such as hemochromatosis, or other iron overload condition secondary to other causes, such as repeated transfusions or anemias. In further embodiments, HFE polypeptides are provided for the inhibition of tumor cell growth. In other embodiments, the HFE polypeptides are provided for use in the isolation of HFE binding proteins. The HFE polypeptides of the invention can be full length HFE or some fragment of HFE. Preferably, the HFE polypeptide comprises the extracellular portion of the HFE. The cDNA sequence of HFE (denoted HH or HLA-H in some publications) and amino acid sequence are provided in FIGS. 4 and 5 (Feder, J. N., et al. *Nature Genetics* 13:399-408 (1996); Ruddy et al., *Genome Res.* 7:441-456 (1997), hereby incorporated by reference in their entirety for all purposes).

The HFE protein, as depicted in FIG. 5, is comprised of the following domains: a leader sequence, the a1 domain, the $\alpha$2 domain, the $\alpha$3 domain, the transmembrane domain, and the cytoplasmic tail.

The boundaries for these domains were approximated by comparison to other MHC class I molecules, as indicated in FIG. 5. The boundary of the leader sequence was determined experimentally. The boundaries of the $\alpha$ 1, 2 and 3 domains were deduced from the generalized structure of MHC class 1 proteins as described in Bjorkman et al., *Annu. Rev. Biochem.* 59:253-258 (1990). The boundaries of the transmembrane domain were deduced from the COOH end of the $\alpha$3 boundary, the composition of the hydrophobic amino acids which form the $\alpha$ helix of the transmembrane domain, and a stretch of hydrophilic amino acids RKRQ (shown in bold in the cytoplasmic domain) which define the boundary of the cytoplasmic side of the domain. The cytoplasmic tail is the remaining amino acids, including the hydrophilic (RKRQ) amino acids. Thus, the approximate boundaries of the domains are about 23-114 ($\alpha$1 domain); about 115-205 ($\alpha$2 domain); about 206-297 ($\alpha$3 domain); about 298-329 (transmembrane domain); and about 330-348 (cytoplasmic domain).

This numbering scheme refers to full-length, unprocessed or "immature" HFE protein. The immature protein is processed in the cell by cleaving off a signal (leader) sequence, i.e., residues 1-22. Thus, numbering of the "mature" protein begins at residue 23, renumbering residue 23 as residue "1". For clarity, the numbering scheme of the immature protein is used herein. Cys282Tyr thus refers to residue 282 of the immature protein, and corresponds to Cys260Tyr in the mature protein. His63Asp refers to residue 63 of the immature protein and corresponds to His41Asp in the mature protein.

The α1, 2 and 3 domains constitute the extracellular portion of the protein. In the absence of the transmembrane domain, this portion of the protein is "soluble" when complexed with β-2-microglobulin ($\beta_2$m). This complex is secreted out of the host cell.

Preferred HFE polypeptides include full-length mature HFE; "soluble" HFE, such as residues 23-297; polypeptides comprising His63, such as residues about 52-72; polypeptides comprising the α1 domain (residues about 23-114); polypeptides comprising residues about 262-282; and polypeptides comprising the α3 domain (residues about 206-297).

The HFE polypeptides may be administered with β-2-microglobulin, such as in the form of a complex. In some embodiments, HFE polypeptides greater than about 20 amino acids are administered in a complex with β-2-microglobulin ($\beta_2$m). Preferably, the HFE polypeptide is co-expressed with $\beta_2$m to affect the formation of such a complex.

In some embodiments of the invention, agonists or antagonists of the HFE protein or transferrin receptor are provided. Agonists of the HFE polypeptide, and/or antagonists of the transferrin receptor, are useful, for example, in the treatment of primary or secondary iron overload diseases or syndromes. In some embodiments, antagonists of the HFE polypeptide, or agonists of the transferrin receptor are useful, for example, in the treatment of iron depletion or deficiency diseases or conditions, such anemias, because they result in an increase in iron absorption. Such antagonists or agonists can be antibodies, preferably monoclonal antibodies, directed against the transferrin receptor or extracellular region of the HFE polypeptide.

Preferably, the HFE polypeptides of the invention for use in the treatment of iron overload diseases, as antagonists of TfR, and/or as agonists of HFE are derived from the unaffected or wild-type sequence of HFE, including polymorphic sequences which do not deleteriously affect the function of HFE.

HFE polypeptides comprising Cys282Tyr or His63Asp or other mutation(s) deleteriously affecting the function of HFE are useful, for example, as antagonists of HFE and/or as agonists of TfR in the treatment of iron deficiency diseases.

In some embodiments of the invention, HFE polypeptides can serve as antagonists of the transferrin receptor. In further embodiments of the invention, peptidomimetics can be designed using techniques well known in the art as antagonists or agonists of the HFE protein and/or the transferrin receptor.

In some embodiments, antisense antagonists of HFE or TfR expression are provided. For a review of the design considerations and use of antisense oligonucleotides, see Uhlmann et al. *Chemical Reviews* 90:543-584 (1990) the disclosure of which is hereby incorporated by reference. The antisense oligonucleotides of the present invention may be synthesized by any of the known chemical oligonucleotide synthesis methods. Such methods are generally described, for example, in Winnacker *From Genes to Clones: Introduction to Gene Technology*, VCH Verlagsgesellschaft mhH (H. Ibelgaufts trans. 1987). Antisense oligonucleotides are advantageously prepared by utilizing any of the commercially available, automated nucleic acid synthesizers. One such device, the Applied Biosystems 380B DNA Synthesizer, utilizes β-cyanoethyl phosphoramidite chemistry.

Since the complete nucleotide sequence of the HFE gene and the complete cDNA sequence of the TfR gene are known, antisense oligonucleotides hybridizable with any portion of their transcripts may be prepared by oligonucleotide synthesis methods known to those skilled in the art. While any length oligonucleotide may be utilized in the practice of the invention, sequences shorter than 12 bases may be less specific in hybridizing to the target mRNA, may be more easily destroyed by enzymatic digestion, and may be destabilized by enzymatic digestion. Hence, oligonucleotides having 12 or more nucleotides are preferred. Long sequences, particularly sequences longer than about 40 nucleotides, may be somewhat less effective in inhibiting translation because of decreased uptake by the target cell. Thus, oligomers of 12-40 nucleotides are preferred, more preferably 15-30 nucleotides, most preferably 18-26 nucleotides. Sequences of 18-24 nucleotides are most particularly preferred.

The transferrin receptor antagonists of the invention, such as the HFE polypeptides of the invention, are useful in the inhibition of tumor cell growth, such as in but not limited to nonsmall cell lung cancer (Carbognani et al., *Cancer* 78:178-179 (1996)), breast cancer (*J. Canc. Res. Clin. Oncol.* 110:71-76 (1985)), prostate cancer (Keer et al., *J. Urology* 143:381-385 (1990)), and testes cancer (Petrylak et al., *J. Natl. Can. Inst.* 86:636-637 (1994)).

Candidate ligands for the transferrin receptor, whether antagonists or agonists, can be screened using the techniques described herein for the ability to bind to the transferrin receptor. Additionally, competition for HFE binding to the receptor can be done using techniques well known in the art. Ligands, or more generally, binding partners for the HFE polypeptide can be screened, for example, for the ability to inhibit the complexing of the HFE polypeptide to β-2-microglobulin, using techniques described herein.

In some embodiments of the invention, agonists or antagonists of transferrin are similarly utilized to increase or decrease the amount of iron transported into a cell, such as into, for example, a patient's hepatocytes, gut epithelial cells, or lymphocytes.

The efficacy of a drug, therapeutic agent, agonist, or antagonist can be identified in a screening program in which modulation is monitored in in vitro cell systems. Host cell systems which express various wild type or mutant HFE proteins (especially the Cys282Tyr and His63Asp mutations (also referred to respectively as 24d1 and 24d2 herein)) are suited for use as primary screening systems. Candidate drugs can be evaluated by incubation with these cells and measuring cellular functions dependent on the HFE gene or by measuring proper HFE protein folding or processing. Such assays might also entail measuring receptor-like activity, iron transport and metabolism, gene transcription or other upstream or downstream biological function as dictated by studies of HFE gene function.

Alternatively, cell-free systems can also be utilized. Purified HFE protein can be reconstituted into artificial membranes or vesicles and drugs screened in a cell-free system. Such systems are often more convenient and are inherently more amenable to high throughput types of screening and automation.

In general, DNA encoding an HFE polypeptide of interest is provided in a mammalian expression vector comprising the following elements linked sequentially at appropriate distances for functional expression: a promoter, an initiation site for transcription, a 5' mRNA leader sequence, a nucleic acid sequence encoding an HFE polypeptide of interest, a 3' untranslated region, and a polyadenylation signal. Enhancer sequences and other sequences aiding expression and/or secretion can also be included in the expression vector. Typically, the HFE signal sequence (encoding amino acids 1 to 22) is retained in the construct to direct secretion of the HFE polypeptide. Additional genes, although signal sequences from other proteins may also be used such as those encoding drug resistance, can be included to allow selection or screening for the presence of the recombinant vector. Such additional genes can include, for example, genes encoding neomycin resistance, multi-drug resistance, thymidine kinase, beta-galactosidase, dihydrofolate reductase (DHFR), and chloramphenicol acetyl transferase. Production of the soluble versions of cell surface molecules structurally related to HFE in a mammalian system has been reported (Gastinel et al., *Proc. Natl. Acad. Sci. U.S.A.* 89:638-642 (1992)). Soluble HFE can also be produced in other cell systems including but not limited to bacterial production systems (see, for example, Altman et al., *Science* 274:94-96 (1996)). In some embodiments HFE and $\beta_2$m can be produced separately and a complex generated by mixing (ibid).

In some embodiments, a GPI (glycophosphatidyl inositol) addition signal is used to replacing the HFE transmembrane domain, so that the HFE polypeptide is expressed on the cell surface as a lipid linked form. Such molecules can be recovered from the soluble fraction after treatment with phosphatidylinositol specific phospholipases to release them from the cell surface (Wettstein et al., *J. Exp. Med.* 174: 219-228 (1991), Lin et al., *Science* 249:677-679 (1990)).

In some embodiments of the invention, the HFE polypeptide of interest is coexpressed with $\beta_2$m in a host cell. The $\beta_2$m gene can be provided on the same expression vector as the HFE gene or may be provided separately, such as on a second expression vector. Thus, for example, an example of an expression construct is as follows. This construct has the following elements in a single expression vector: leader sequence and $\alpha_1$, $\alpha_2$ and $\alpha_3$ domains of HFE which contain the whole extracellular domain and signal sequence attached with a CMV (cytomegalovirus) promoter and bovine growth hormone (BGH) polyadenylation signal, both derived from pcDNA3.1 (Invitrogen, Inc.); the whole coding sequence of human β2 microglobulin gene expressed under the control of the chicken β-actin promoter, the CMV-IE enhancer, and the rabbit β-globin polyadenylation signal, all derived from pCAGGS (Miyazaki et al., *Gene* 79:269-277 (1989)); and a 1.8 kb EcoRI-BglII fragment derived from the mouse dihydrofolate reductase (dhfr) gene which contains the entire coding sequence, promoter and methotrexate responsive dhfr amplicon. This construct can be introduced into DHFR negative tissue culture cells using standard transfection protocols (e.g., Sambrook et al. *Molecular Cloning: A Laboratory Manual* (Cold Spring Harbor Laboratory, Cold Spring Harbor, N.Y. (1989)) and selected for methotrexate resistance. Selection by stepwise increasing concentrations of methotrexate causes an amplification of this expression vector to achieve a high copy number of this vector in a cell.

In some embodiments, soluble HFE is expressed as a fusion protein using an expression vector which contains a fusion partner, such as EGFP (a variant of green fluorescent protein (GFP)). For example, leader sequence and $\alpha_1$, $\alpha_2$, and $\alpha_3$ domains of HFE cDNA which contain the whole extracellular domain and signal sequence can be inserted into the KpnI/BamHI cloning site in the pEGFP-N3 vector (Clontech, Inc.). $\beta_2$m can be provided as part of the same or a second vector within the host cell.

In some embodiments of the invention, the HFE polypeptide is expressed as a soluble complex with $\beta_2$m and purified from culture medium. In other embodiments of the invention, the HFE protein can be purified by one of several methods which have been selected based upon the molecular properties revealed by its sequence and its homology to MHC Class I molecules. Since the molecule possesses properties of an integral membrane protein, i.e. contains a transmembrane domain, the protein is preferably first isolated from the membrane fraction of cells using detergent solubilization. A variety of detergents useful for this purpose are well known in the art.

Once solubilized, the HFE protein can be further purified by conventional affinity chromatography techniques. The conventional approaches of ion exchange, hydrophobic interaction, and/or organomercurial chromatographies can be utilized. These methodologies take advantage of natural features of the primary structure, such as: charged amino acid residues, hydrophobic transmembrane domains, and sulfhydryl-containing cysteine residues, respectively. In the affinity chromatography approach use is made of immunoaffinity ligands or of the proposed interaction of the HFE protein with β-2-microglobulin, transferrin receptor, calnexin or similar molecules. In the former, the affinity matrix consists of antibodies (polyclonal or monoclonal) specific to the HFE protein coupled to an inert matrix. The production of antibodies specific to the HFE protein can be performed using techniques well known in the art. In the latter method, various ligands which are proposed to specifically interact with the HFE protein based on its homology with MHC Class I molecules could be immobilized on an inert matrix. For example, β-2-microglobulin, β-2-microglobulin-like molecules, or other specific proteins such as calnexin or calnexin-like molecules, the transferrin receptor and the like, or portions and/or fragments thereof, can be utilized. General methods for preparation and use of affinity matrices are well known in the art.

Criteria for the determination of the purity of the HFE protein include those standard to the field of protein chemistry. These include N-terminal amino acid determination, one and two-dimensional polyacrylamide gel electrophoresis, and silver staining. The purified protein is useful for use in studies related to the determination of secondary and tertiary structure, as aid in drug design, and for in vitro study of the biological function of the molecule.

In some embodiments of the invention, drugs can be designed to modulate HFE gene and HFE protein activity from knowledge of the structure and function correlations of HFE protein and from knowledge of the specific defect in various HFE mutant proteins. For this, rational drug design by use of X-ray crystallography, computer-aided molecular modeling (CAMM), quantitative or qualitative structure-activity relationship (QSAR), and similar technologies can further focus drug discovery efforts. Rational design allows prediction of protein or synthetic structures which can interact with and modify the HFE protein activity. Such structures may be synthesized chemically or expressed in biological systems. This approach has been reviewed in Capsey et al., Genetically Engineered Human Therapeutic Drugs, Stockton Press, New York (1988). Further, combinatorial libraries can be designed, synthesized and used in screening programs.

In order to administer therapeutic agents based on, or derived from, the present invention, it will be appreciated that suitable carriers, excipients, and other agents may be incorporated into the formulations to provide improved transfer, delivery, tolerance, and the like.

A multitude of appropriate formulations can be found in the formulary known to all pharmaceutical chemists: Remington's Pharmaceutical Sciences, (15th Edition, Mack Publishing Company, Easton, Pa. (1975)), particularly Chapter 87, by Blaug, Seymour, therein. These formulations include for example, powders, pastes, ointments, jelly, waxes, oils, lipids, anhydrous absorption bases, oil-in-water or water-in-oil emulsions, emulsions carbowax (polyethylene glycols of a variety of molecular weights), semi-solid gels, and semi-solid mixtures containing carbowax.

Any of the foregoing formulations may be appropriate in treatments and therapies in accordance with the present invention, provided that the active agent in the formulation is not inactivated by the formulation and the formulation is physiologically compatible.

The present invention also relates to the use of polypeptide or protein replacement therapy for those individuals determined to have a defective HFE gene. Treatment of HH disease can be performed by replacing the defective HFE protein with normal protein or its functional equivalent in therapeutic amounts. A therapeutically effective amount of an HFE polypeptide for "replacement therapy", an HFE agonist, or transferrin receptor antagonist is an amount sufficient to decrease the amount of iron transported into a cell. The cell may be, for example, a lymphocyte, epithelial cell, or hepatocyte.

Similarly, a therapeutically effective amount of an HFE antagonist or transferrin receptor agonist is an amount sufficient to increase the amount of iron transported into a cell.

HFE polypeptide can be prepared for therapy by any of several conventional procedures. First, HFE polypeptide can be produced by cloning the HFE cDNA into an appropriate expression vector, expressing the HFE gene product from this vector in an in vitro expression system (cell-free or cell-based) and isolating the HFE protein from the medium or cells of the expression system. General expression vectors and systems are well known in the art. In addition, the invention envisions the potential need to express a stable form of the HFE protein in order to obtain high yields and obtain a form readily amenable to intravenous administration. Stable high yield expression of proteins have been achieved through systems utilizing lipid-linked forms of proteins as described in Wettstein et al. *J Exp Med* 174:219-228 (1991) and Lin et al. *Science* 249:677-679 (1990).

HFE protein or portions thereof can be prepared synthetically. Alternatively, the HFE protein can be prepared from total protein samples by affinity chromatography. Sources would include tissues expressing normal HFE protein, in vitro systems (outlined above), or synthetic materials. The affinity matrix would consist of antibodies (polyclonal or monoclonal) coupled to an inert matrix. In addition, various ligands which specifically interact with the HFE protein could be immobilized on an inert matrix, such as β-2-microglobulin or portions thereof, β-2-microglobulin-like molecules, or other specific proteins such as calnexin and calnexin-like molecules or portions thereof. General methods for preparation and use of affinity matrices are well known in the art.

Protein replacement therapy requires that HFE polypeptides be administered in an appropriate formulation. The HFE polypeptides can be formulated in conventional ways standard to the art for the administration of protein substances. Delivery may require packaging in lipid-containing vesicles (such as LIPOFECTIN™ or other cationic or anionic lipid or certain surfactant proteins) that facilitate incorporation into the cell membrane. The HFE protein formulations can be delivered to affected tissues by different methods depending on the affected tissue. For example, iron absorption is initiated in the GI tract. Therefore, delivery by catheter or other means to bypass the stomach would be desirable. In other tissues, intravenous (IV) is preferred.

In a further embodiment of the invention, a method is provided for diagnosing an iron misregulation disease, wherein nucleic acid from a patient is screened for mutations in the transferrin receptor gene that, for example, prevent or mitigate the binding of the transferrin receptor to HFE. Without being limited to any one theory, such mutations in TfR would be diagnostic of an iron overload-causing situation where too much iron-bound transferrin is brought into the cell. The nucleotide sequence of the human transferrin receptor gene was disclosed by McClelland et al., *Cell* 39:267-274 (1984) which is hereby incorporated by reference in its entirety for all purposes.

In a further embodiment of the invention, a method is provided for diagnosing an iron misregulation disease, wherein nucleic acid from a patient is screened for mutations in the transferrin gene that, for example, effect the affinity of transferrin for the transferrin receptor. Without being limited to any one theory, such mutations could overcome the negative effect of HFE and allow high affinity ligand binding even in the presence of normal HFE. The nucleotide sequence of the human transferrin gene is disclosed in Schaeffer et al., *Gene* 56:109-116 (1987), which is hereby incorporated by reference in its entirety for all purposes.

Methods of screening nucleic acid for mutations are well known in the art, including, but not limited to, restriction-fragment-length-polymorphism detection based on allele-specific restriction-endonuclease cleavage (Kan and Dozy *Lancet* ii:910-912 (1978)), hybridization with allele-specific oligonucleotide probes (Wallace et al. *Nucl Acids Res* 6:3543-3557 (1978)), including immobilized oligonucleotides (Saiki et al. *Proc. Natl. Acad. Sci. U.S.A.* 86:6230-6234 (1989)) or oligonucleotide arrays (Maskos and Southern *Nucl Acids Res* 21:2269-2270 (1993)), allele-specific PCR (Newton et al. *Nucl Acids Res* 17:2503-2516 (1989)), mismatch-repair detection (MRD) (Faham and Cox *Genome Res* 5:474-482 (1995)), binding of MutS protein (Wagner et al. *Nucl Acids Res* 23:3944-3948 (1995), denaturing-gradient gel electrophoresis (DGGE) (Fisher and Lerman et al. *Proc. Natl. Acad. Sci. U.S.A.* 80:1579-1583 (1983)), single-strand-conformation-polymorphism detection (Orita et al. *Genomics* 5:874-879 (1983)), RNAase cleavage at mismatched base-pairs (Myers et al. *Science* 230:1242 (1985)), chemical (Cotton et al. *Proc. Natl. Acad. Sci. U.S.A.* 85:4397-4401 (1988)) or enzymatic (Youil et al. *Proc. Natl. Acad. Sci. U.S.A.* 92:87-91 (1995)) cleavage of heteroduplex DNA, methods based on allele specific primer extension (Syvänen et al. *Genomics* 8:684-692 (1990)), genetic bit analysis (GBA) (Nikiforov et al. *Nucl Acids Res* 22:4167-4175 (1994)), the oligonucleotide-ligation assay (OLA) (Landegren et al. *Science* 241:1077 (1988)), the allele-specific ligation chain reaction (LCR) (Barrany *Proc. Natl. Acad. Sci. U.S.A.* 88:189-193 (1991)), gap-LCR (Abravaya et al. *Nucl Acids Res* 23:675-682 (1995)), and radioactive and/or fluorescent DNA sequencing using standard procedures well known in the art.

In further embodiments of the invention, HFE/$\beta_2$m heterodimers are used to screen for proteins or small molecules having affinity for the complex. Methods to find such proteins are well known and include affinity chromatography applications whereby HFE/$\beta_2$m heterodimers coupled to a column are used to screen and select proteins and small molecules. For example, a known soluble form of TfR (see Cook et al., *Annu. Rev. Med.* 44: 63-74 (1993)) is expected to bind the HFE/$\beta_2$m complex. Binding molecules can also be detected by eluting the bound proteins and running the eluate on PAGE followed by protein staining. Alternatively, various protein cross-linkers may be used to irreversibly bind transient and weakly associating proteins to HFE/TfR complex either on or in the cell (see, for example, Waugh et al., *Biochem.* 28:3448-3455 (1989)).

In some embodiments, yeast two-hybrid systems are used to isolate proteins which interact specifically with the cytoplasmic portion of the HFE protein (see for example, Brent et al., *Nature* 312:612-615 (1984); Brent et al., *Cell* 43:729-736 (1985); Chien et al., *Proc. Natl. Acad. Sci. U.S.A.* 88:9578-9582 (1991)). It is this part of the protein that in other systems, is known to direct the subcellular localization of protein that traffic from the cell surface and through the cell (see, for example, Weiser et al., *Science* 276:407-409 (1997); Williams et al., *J. Cell Biol.* 111:955-966 (1990); Marks et al., *J. Cell Biol.* 131:351-369 (1995); Letourneur et al., *Cell* 69:1143-1157 (1992); Sugita et al., *Science* 273: 349-352 (1996); Voorhees et al., *EMBO J.* 14:4961-4975 (1995)). HFE/$\beta_2$m associating proteins isolated by these methods may effect the rate of internalization of either molecule having a role in controlling iron uptake.

Preferably, these analyses are performed using samples of serum, nucleic acid, tissue, etc., from individuals that exhibit iron overloading but do not have either of the two described mutations in the HFE gene (Feder et al., *Nature Genetics* 13:399-408). Genes encoding the HFE/$\beta_2$m associating proteins and mutations thereon would constitute additional diagnostic targets for iron misregulation diseases.

In an embodiment of the invention, a transferrin binding assay is provided for the diagnosis of iron misregulation diseases. Typically, the assay is carried out on blood, intestinal or liver biopsy material, from normal individuals and patients, whereby cells are incubated in the presence of different concentrations of $^{125}$I-transferrin (the ligand). After a period of time, the cells are centrifuged through a matrix to separate the cells from the free ligand. Both the label in the cells (bound) and the media (free) is counted. From these data, estimates to the molar amounts of transferrin bound by the cells and that left in solution are made, subjected to Scatchard analysis, and estimates of the dissociation constants ($K_D$) made. Normal individuals would have a high $K_D$ value representing low affinity for transferrin. Affected individuals, for example, would have lower $K_D$ values representing higher affinity for transferrin. Similar types of transferrin binding assays have been previously described (Ward, J. H., et al. *J. Biol. Chem.* 257: 10317-10323 (1982), Klausner, R. D. et al., *J. Biol. Chem.* 258: 4715-4724 (1983), Mulford and Lodish, *J. Biol. Chem.* 263: 5444-5461 (1988)).

Gene therapy utilizing recombinant DNA technology to deliver nucleic acids encoding HFE polypeptides, transferrin receptor polypeptides, transferrin polypeptides, or antagonists or agonists of HFE, transferrin receptor, or transferrin into patient cells or vectors which will supply the patient with gene product in vivo is also contemplated within the scope of the present invention.

Gene therapy techniques have the potential for limiting the exposure of a subject to a gene product, such as an HFE polypeptide, by targeting the expression of the therapeutic gene to a tissue of interest, such as hepatocytes, intestinal epithelium, etc. For example, WIPO Patent Application Publication No. WO 93/15609 discloses the delivery of interferon genes to vascular tissue by administration of such genes to areas of vessel wall injury using a catheter system. In another example, an adenoviral vector encoding a protein capable of enzymatically converting a prodrug, a "suicide gene", and a gene encoding a cytokine are administered directly into a solid tumor.

Other methods of targeting therapeutic genes to tissues of interest include the three general categories of transductional targeting, positional targeting, and transcriptional targeting (for a review, see, e.g., Miller et al. *FASEB J.* 9:190-199 (1995)). Transductional targeting refers to the selective entry into specific cells, achieved primarily by selection of a receptor ligand. Positional targeting within the genome refers to integration into desirable loci, such as active regions of chromatin, or through homologous recombination with an endogenous nucleotide sequence such as a target gene. Transcriptional targeting refers to selective expression attained by the incorporation of transcriptional promoters with highly specific regulation of gene expression tailored to the cells of interest.

Examples of tissue-specific promoters include a liver-specific promoter (Zou et al. *Endocrinology* 138:1771-1774 (1997)); a small intestine-specific promoter (Olivera et al. *J. Biol. Chem.* 271:31831-31838 (1996)); the promoter for creatine kinase, which has been used to direct the expression of dystrophin cDNA expression in muscle and cardiac tissue (Cox et al. *Nature* 364:725-729 (1993)); and immunoglobulin heavy or light chain promoters for the expression of suicide genes in B cells (Maxwell et al. *Cancer Res.* 51:4299-4304 (1991)). An endothelial cell-specific regulatory region has also been characterized (Jahroudi et al. *Mol. Cell. Biol.* 14:999-1008 (1994)). Amphotrophic retroviral vectors have been constructed carrying a herpes simplex virus thymidine kinase gene under the control of either the albumin or alpha-fetoprotein promoters (Huber et al. *Proc. Natl. Acad. Sci. U.S.A.* 88:8039-8043 (1991)) to target cells of liver lineage and hepatoma cells, respectively. Such tissue specific promoters can be used in retroviral vectors (Hartzoglou et al. *J. Biol. Chem.* 265:17285-17293 (1990)) and adenovirus vectors (Friedman et al. *Mol. Cell. Biol.* 6:3791-3797 (1986)) and still retain their tissue specificity.

Other elements aiding specificity of expression in a tissue of interest can include secretion leader sequences, enhancers, nuclear localization signals, endosmolytic peptides, etc. Preferably, these elements are derived from the tissue of interest to aid specificity.

Viral vector systems useful in the practice of the instant invention include but are not limited to adenovirus, herpesvirus, adeno-associated virus, minute virus of mice (MVM), HIV, sindbis virus, and retroviruses such as Rous sarcoma virus, and MoMLV. Typically, the nucleic acid encoding the therapeutic polypeptide of interest is inserted into such vectors to allow packaging of the nucleic acid, typically with accompanying viral DNA, infection of a sensitive host cell, and expression of the polypeptide of interest.

In still other embodiments of the invention, nucleic acid encoding a therapeutic polypeptide of interest is conjugated to a cell receptor ligand for facilitated uptake (e.g., invagination of coated pits and internalization of the endosome) through a DNA linking moiety (Wu et al. *J. Biol. Chem.* 263:14621-14624 (1988); WO 92/06180). For example, the DNA constructs of the invention can be linked through a polylysine moiety to asialo-oromucoid, which is a ligand for the asialoglycoprotein receptor of hepatocytes.

Similarly, viral envelopes used for packaging the recombinant constructs of the invention can be modified by the addition of receptor ligands or antibodies specific for a receptor to permit receptor-mediated endocytosis into specific cells (e.g., WO 93/20221, WO 93/14188; WO 94/06923). In some embodiments of the invention, the DNA constructs of the invention are linked to viral proteins, such as adenovirus particles, to facilitate endocytosis (Curiel et al. *Proc. Natl. Acad. Sci. U.S.A.* 88:8850-8854 (1991)). In other embodiments, molecular conjugates of the instant invention can include microtubule inhibitors (WO/9406922); synthetic peptides mimicking influenza virus hemagglutinin (Plank et al. *J. Biol. Chem.* 269:12918-12924 (1994)); and nuclear localization signals such as SV40 T antigen (WO93/19768).

The nucleic acid can be introduced into the tissue of interest in vivo or ex vivo by a variety of methods. In some embodiments of the invention, the nucleic acid is introduced to cells by such methods as microinjection, calcium phosphate precipitation, liposome fusion, or biolistics. In further embodiments, the nucleic acid is taken up directly by the tissue of interest. In other embodiments, nucleic acid is packaged into a viral vector system to facilitate introduction into cells.

In some embodiments of the invention, the compositions of the invention are administered ex vivo to cells or tissues explanted from a patient, then returned to the patient. Examples of ex vivo administration of gene therapy constructs include Arteaga et al. *Cancer Research* 56(5):1098-1103 (1996); Nolta et al. *Proc Natl. Acad. Sci. USA* 93(6): 2414-9 (1996); Koc et al. *Seminars in Oncology* 23 (1):46-65 (1996); Raper et al. *Annals of Surgery* 223(2):116-26 (1996); Dalesandro et al. *J. Thorac. Cardi. Surg.* 11(2):416-22 (1996); and Makarov et al. *Proc. Natl. Acad. Sci. USA* 93(1):402-6 (1996).

The following examples are provided to illustrate certain aspects of the present invention and not intended as limiting the subject matter thereof.

EXPERIMENTAL EXAMPLES

I. Interaction of HFE with the Transferrin Receptor (TfR)

A. Introduction

In this experimental example, we demonstrated that HFE forms a stable complex with the transferrin receptor (TfR), the molecule responsible for receptor-mediated endocytosis of iron-bound transferrin. This interaction, assessed both in cultured cells by over-expression of HFE and also by addition of soluble HFE/$\beta_2$m heterodimers, causes a decrease in the apparent affinity of the TfR for transferrin. In contrast, the disease-causing mutation (Cys282Tyr) fails to form this TfR complex permitting high affinity binding of transferrin. These results established the first molecular link between HFE and iron absorption and indicate that an altered regulation of transferrin-dependent iron uptake leads to hemochromatosis disease.

B. Methods

1. Cell surface protein biotinylations. Cells (4×10$^6$) were seeded into 100 mm dishes and grown overnight to 80% confluency. The plates were moved to 4° C. and gently washed four times with PBS. Suflo-NHS-LC Biotin (Pierce) was added in PBS to a final concentration of 500 µg/ml and incubated on ice for 30 mins. The Biotin reagent was removed and the plates washed four times with PBS containing 50 mM glycine. Cells were lysed in 500 ml of 25 mM Tris-HCl, pH 7.5/150 mM NaCl/0.5% NP-40. Protein concentrations were determined by BCA assay (Pierce) and one mg of protein was pre-cleared with Protein-G-Sepharose (Pharmacia) and immunoprecipitated with either 10 µg of anti-HFE rabbit polyclonal antibody (CT1) (Feder, J. N., et al. *J. Biol. Chem.* 272:14025-14028 (1997)), 50 µg of FLAG (M2) monoclonal antibody (Kodak), 5 µg of transferrin receptor monoclonal antibody (Caltag) or 10 µg of HLA-ABC antibody (Immunotech). Precipitated proteins were separated on 4-20% Tris-glycine polyacrylamide gels (Novex), electroblotted to PVDF membranes (Novex) and biotinylated proteins were visualized with 2 µg/ml of streptavidin-HRP (Pierce) followed by ECL detection reagents (Amersham).

2. Immunoprecipations and western blotting. Cells were lysed in the same buffer as above and precipitations carried out with the same antibodies and concentrations except that no pre-clearing step was carried out. Precipitated proteins were separated and electroblotted to PVDF membranes as previously described (Feder, J. N., et al. *J. Biol. Chem.* 272:14025-14028 (1997).

3. Transferrin binding assays. Transferrin binding assays were carried out as essentially as described (Ward, J. H. et al., *J. Biol. Chem.* 257:10317-10323 (1982)) with the following modifications. Cells were seeded at a density of 6×10$^5$ per well in 6-well dishes coated with 0.01% fibronectin (Sigma) and grown overnight. Cells were washed once with 2 ml of DME-H21 media containing 1% FBS and then incubated at either 37° C. or on ice with varying concentrations of transferrin which include [$^{125}$I]-diferric transferrin (1 mCi/mg) (New England nuclear) as a tracer ($^1$/$_{30}$$^{th}$ of the final concentration) in a final volume of 750 µl. To determine the amount of non-specific transferrin binding, cells were simultaneously incubated under the same conditions but in the presence of 100 times the molar concentration of cold holo-transferrin (Sigma). After 20 mins (37° C.) or 90 mins (4° C.), the medium was removed and counted in a Beckman 9600 scintillation counter. The cells were incubated on ice and washed twice with medium containing 1% FBS, and then lysed with 1% SDS and counted. Specific binding was calculated by substracting the non-specific binding from the total binding. A second method was also used that utilized a constant amount of labeled transferrin (10 nM) and increasing amount of unlabeled transferrin to increase the total transferrin concentration. Identical results to those produced by the first method were obtained.

4. Expression and Purification of Secreted HFE.

A secreted HFE/$\beta_2$m heterodimer was constructed as follows, wherein the amino acid sequence of the HFE was:

```
                                              (SEQ ID NO:8)
RLLRSHSLHYLFMGASEQDLGLSLFEALGYVDDQLFVFYDHESRRVEPRT

PWVSSRISSQMWLQLSQSLKGWDHMFTVDFWTIMENHNHSKESHTLQVIL

GCEMQEDNSTEGYWKYGYDGQDHLEFCPDTLDWRAAEPRAWPTKLEWERH

KIRARQNRAYLERDCPAQLQQLLELGRGVLDQQVPPLVKVTHHVTSSVTT

LRCRALNYYPQNITMKWLKDKQPMDAKEFEPKDVLPNGDGTYQGWITLAV

PPGEEQRYTCQVEHPGLDQPLIVIWE.
```

A 5' Xho I site, a stop codon after the codon corresponding to amino acid 298 (residue 276 of the mature protein) and a 3' Not I site were inserted in the HFE gene by site-directed mutagenesis. After verifying the sequence, the modified HFE gene was subcloned into the expression vector PBJ5-GS that carries the glutamine synthetase gene as a selectable marker and as a means of gene amplification in the presence of the drug methionine sulfoximine (Bebbingtion, C. R. & Hentschel, C. G. G. in *DNA Cloning: A Practical Approach*. (ed. Glove, DM) 163-188 (Oxford: IL, 1987)). The HFE expression plasmid was cotransfected with a human $\beta_2$m expression vector (i.e., full length, wild type $\beta_2$m, Fahnestock, M. L., et al. *Immunity* 3:583-590 (1995)) into CHO cells. Cell lines secreting HFE/$\beta_2$m heterodimers were identified by immunoprecipitation of supernatants of $^{35}$S-methionine metabolically labeled cells using an antibody against human $\beta_2$m (BBM.1) (Parham, P. et al., *J. Biol. Chem.* 258:6179-6186 (1983)). A protein of molecular mass of 43 kDa was co-immunoprecipitated with labeled $\beta_2$m from the supernatants, and was verified to be the truncated HFE polypeptide chain by N-terminal sequencing of the purified protein (yielding the sequences RLLRSHSLHYLF and IQRTPKIQVYSR corresponding to the correctly processed mature forms of HFE and human $\beta_2$m). Soluble HFE/$\beta_2$m heterodimers were purified on a BBM.1 immunoaffinity column, followed by separation of free $\beta_2$m from the heterodimers on a Superdex™ 75 HR 10/30 FPLC gel filtration column or by using an immunoaffinity column constructed with an HFE monoclonal antibody raised against the purified heterodimer. 0.25 mg of purified secreted HFE, FcRn and UL18 were treated with acetic acid and analysed for the presence of bound peptides using established methods (Rotzschke, O., et al. *Nature* 348:252-257 (1990)) as previously described for UL18 (Fahnestock, M. L., et al. *Immunity* 3:583-590 (1995)) and FcRn (Raghavah, M. et al., *Biochemistry* 32:8654-8660 (1993)). Acid eluates were analyzed by Edman degradation using an Applied Biosystems Model 477A protein sequencer for pool sequencing (Table 1). In order to detect N-terminally blocked peptides, the HFE and FcRn eluates were analyzed by matrix-assisted, laser desorption, time-of-flight mass spectrometry using a PersSeptive Biosystems ELITE mass spectrometer.

TABLE 1 pmole of amino acids recovered from acid elutions.

| Cycle number | HFE | FcRn | UL18 |
|---|---|---|---|
| 1 | 2.1 | 5.9 | 86.0 |
| 2 | 0.5 | 4.7 | 75.1 (Leu, Met = 71) |
| 3 | 0.4 | 0.7 | 36.9 (Pro = 19) |
| 4 | 0.8 | 7.6 | 19.8 |
| 5 | 0.0 | 0.0 | 11.3 |
| 6 | 3.5 | 0.0 | 4.0 |
| 7 | 1.0 | 0.2 | 3.7 |
| 8 | 0.0 | 0.6 | 6.5 |
| 9 | 1.9 | 9.5 | 4.3 |
| 10 | 0.0 | 0.3 | 1.3 |

The total yield of amino acids from each sequencing cycle is presented for acid eluates derived from equivalent amount of soluble HFE, FcRN and UL18 heterodimers. Only those amino acid residues that showed an increase in the absolute amount recovered compared to the previous cycle were considered significant. Results for the FcRn and UL18 eluates are similar to those previously reported (Fahnestock, M. L., et al. Immunity 3: 583-590 (1995); Raghavah, M. et al., Biochemistry 32: 8654-8660 (1993)) in which UL18, but not FcRn, was shown to bind endogenous peptides.

C. Results and Discussion

To investigate the role of HFE in the regulation of iron metabolism, we utilized cell-surface labeling to detect potential HFE interactive proteins. Human embryonic kidney cells (293 cells), engineered to over-express either wild-type or mutant forms of HFE, were treated with biotin-conjugated N-hydroxysuccinimide (NHS-biotin) to label proteins expressed on the cell-surface. Subsequently, total cell lysates were immunoprecipitated with previously characterized antibodies directed toward the C-terminal peptide sequence of HFE or monoclonal antibodies against the FLAG epitope tag which had been engineered into the HFE protein (Feder, J. N., et al. *J. Biol. Chem.* 272:14025-14028 (1997)). Biotinylated proteins were detected with streptavidin-conjugated horseradish peroxidase (HRP). Lysates from parental 293 cells displayed little surface-labeling in accordance with previous results, demonstrating undetectable levels of HFE protein in these cells (FIGS. 1A and B) (Feder, J. N., et al. *J. Biol. Chem.* 272:14025-14028 (1997)). In contrast, prominent bands of 12, 49, 100 and 200 kDa were observed in lysates from cells overexpressing the wild-type HFE; these bands were absent from immunoprecipitates from cells overexpressing the Cys282Tyr mutant form of HFE (FIGS. 1A and B). Previous studies demonstrated that the plasma membrane-bound form of HFE was 49 kDa in molecular mass and associated with $\beta_2$m, a 12 kDa protein (Feder, J. N., et al. *J. Biol. Chem.* 272:14025-14028 (1997)). The presence of 49 and 12 kDa labeled bands in HFE-specific immune-complexes from wild-type HFE expressing cells and their absence in parental and Cys282Tyr mutant expressing cells is consistent with their identity as HFE and $\beta_2$m. The failure of the 100 and 200 kDa proteins to be co-immunoprecipitated from the Cys282Tyr mutant expressing cells indicates a specific interaction of these proteins with the cell-surface form of HFE.

To determine the specificity of these protein interactions with HFE, we performed immunoprecipitations with antibodies that recognize the related HLA-A, B and C proteins. These antibodies detected proteins at approximately 45 kDa and 12 kDa, the predicted molecular masses of HLA heavy chain and $\beta_2$m, but failed to co-immunoprecipitate the 100 and 200 kDa bands (FIG. 1D).

To identify the 100 and 200 kDa proteins which co-immunoprecipitated with HFE, we investigated proteins known to participate in iron homeostasis. Interestingly, the transferrin receptor (TfR), the major carrier of transferrin-bound iron, is known to display a characteristic pattern of monomers and dimers migrating at approximately 100 and 200 kDa in denaturing gel electrophoresis (Seligman, P. A. et al. *J. Biol. Chem.* 254:9943-9946 (1979); Wada, H. G. et al., *J. Biol. Chem.* 254:12629-12635 (1979); Omary, M. B. et al., *J. Biol. Chem.* 256:12888-12892 (1981)). To determine whether HFE could associate with the TfR, we utilized TfR antibodies to immunoprecipitate surface-labeled proteins from the three cell lines. Two prominent proteins of molecular mass corresponding to the monomeric and dimeric forms of the TfR were seen in the parental 293 as well as the wild-type HFE and the Cys282Tyr mutant HFE expressing cell lines (FIG. 1C). Significantly, two proteins with masses corresponding to those of HFE and $\beta_2$m (49 kDa and 12 kDa, respectively) were observed only in lysates from the cells which overexpress wild-type HFE but not in lysates from the parental 293 or Cys282Tyr mutant protein expressing cells.

Figure 2:
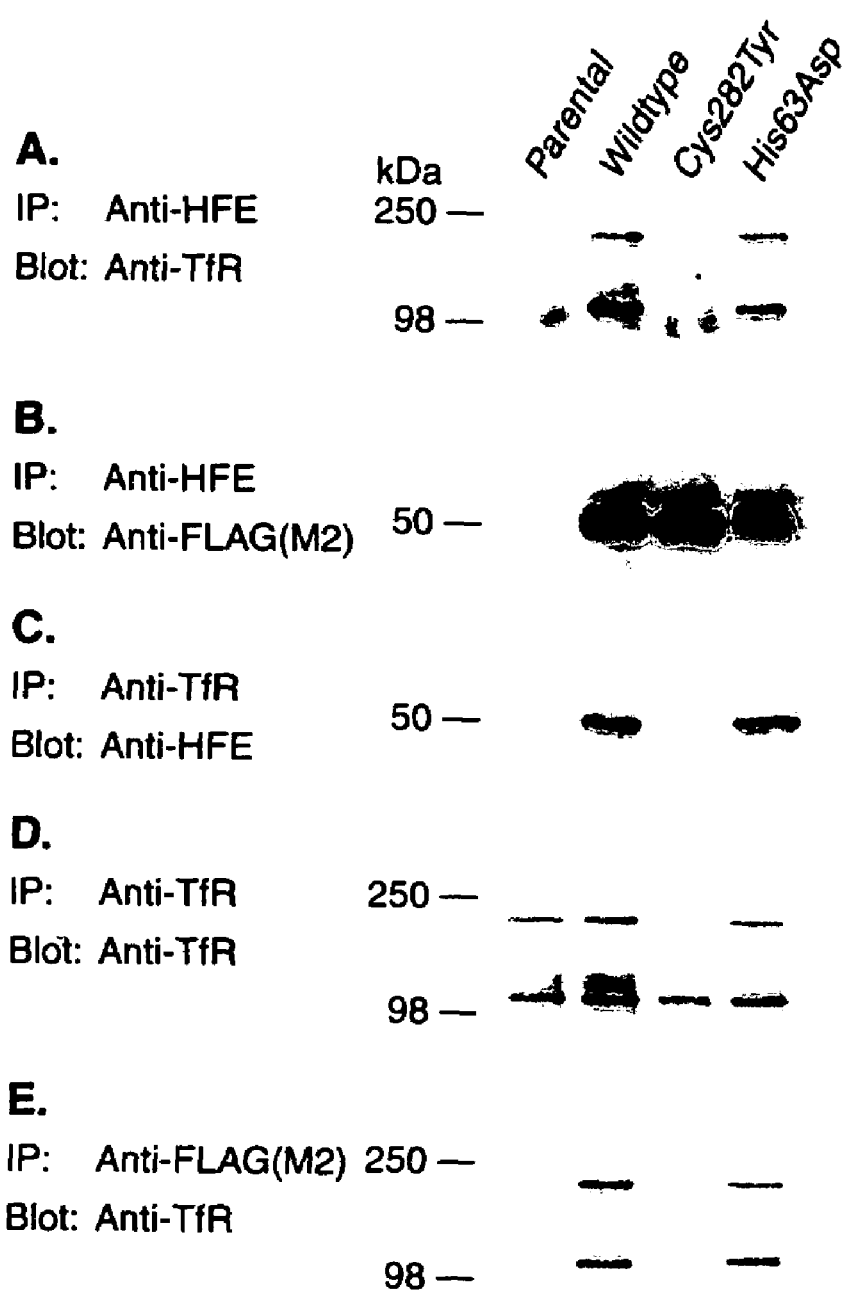
FIG. 2 (A-E). Direct association of TfR with HFE.

The HFE/TfR association results were corroborated by performing co-immunoprecipitation experiments on unlabeled total cell lysates. Immunoprecipitation with HFE antibodies followed by blotting and probing with antibodies to TfR demonstrated that the TfR was complexed only with the wild-type form of HFE but not with the Cys282Tyr mutant (FIG. 2A). Stripping this blot and reprobing with the FLAG epitope antibodies to detect HFE demonstrated that equivalent amounts of HFE were expressed and immunoprecipitated from each of the cell lines but, as expected, were absent in the parental 293 cells (FIG. 2B). Performing the inverse experiment, wherein cell lysates were first immunoprecipitated with TfR antibodies followed by blotting with HFE antibodies, revealed that HFE co-immunoprecipitated with the TfR from the wild-type expressing cells but not the Cys282Tyr or parental 293 cell lines (FIG. 2C). The absence of HFE in the parental 293 and Cys282Tyr mutant cell lines was not due to failure to precipitate TfR; reprobing the blot with TfR antibodies demonstrated that similar amounts of TfR protein were precipitated from each of the cell lines (FIG. 2D). To further control for the specificity of the HFE antibodies, we first immunoprecipitated cell lysates with FLAG epitope antibodies to specifically precipitate the HFE/FLAG fusion proteins followed by blotting with TfR antibodies. As in FIG. 2A, the TfR was co-immunoprecipitated in the wild-type HFE expressing cells but not from the Cys282Tyr mutant expressing cells (FIG. 2E). Experiments performed on an independent series of cell lines engineered to express wild-type and mutant HFE which lacked the FLAG epitope tag yielded identical results to those shown in FIG. 2 when immunoprecipitations were carried out with HFE and TfR antibodies.

In immunoprecipitation experiments on unlabeled cell lysates we included as a further control another mutant of HFE wherein histidine 63 was replaced by aspartate (His63Asp). As with wild-type HFE, the His63Asp protein is also expressed on the cell surface (Feder, J. N., et al. *J. Biol. Chem.* 272:14025-14028 (1997)), however, functional effect of this mutation has yet been identified. The association of HFE with the TfR as assessed by co-immunoprecipitation appeared unaffected by the His63Asp mutation (FIG. 2A-E).

Figure 3A:
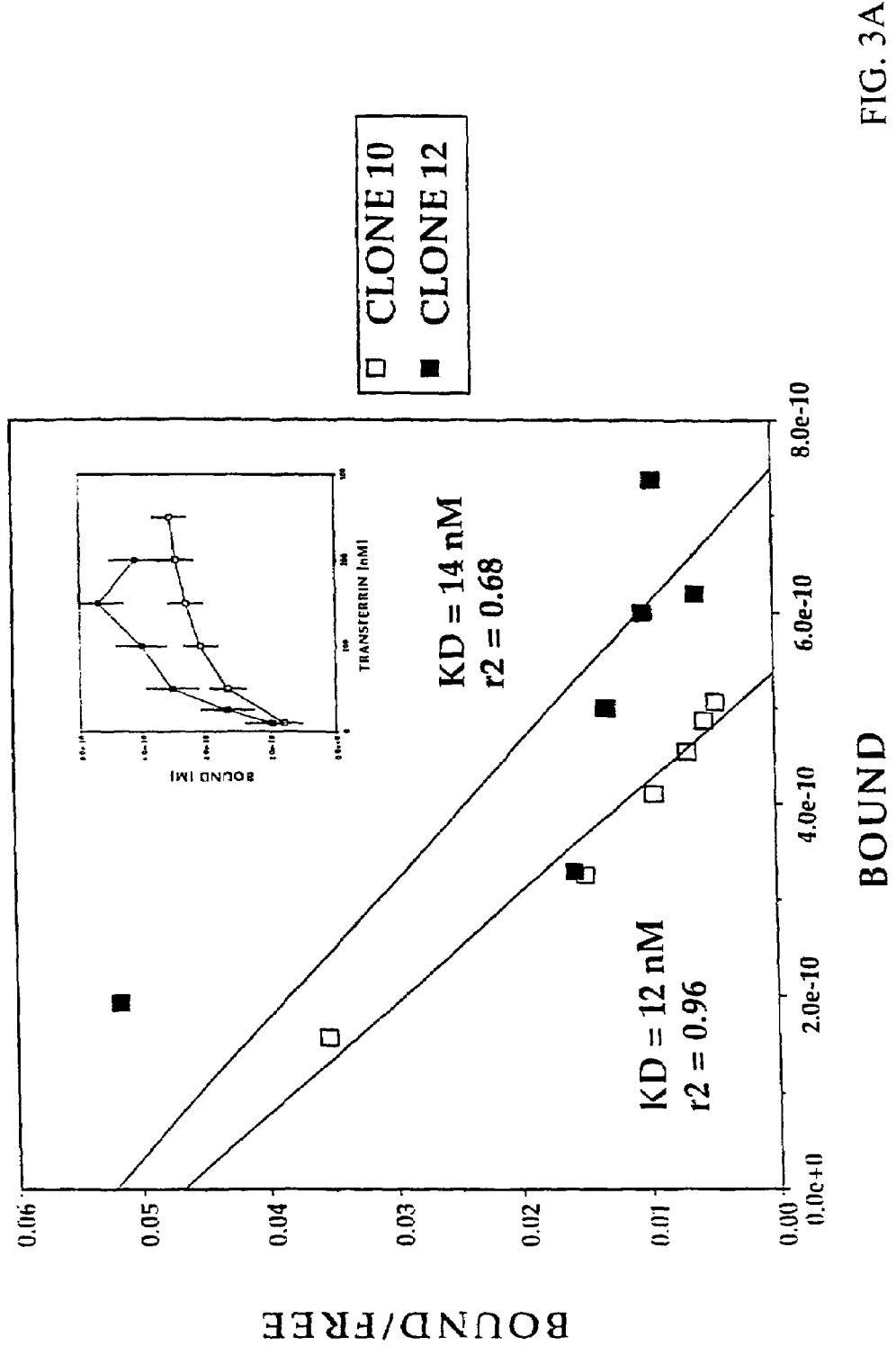
(FIG. 3A) Transferrin binding to TfR in cells that over-express the Cys282Tyr mutant protein (intracellular) (inset). Cells (clone 10, open squares and clone 12, closed squares) were incubated with various concentrations of transferrin at 37° C. for 20 mins. The data represent the mean of duplicate determinations corrected for non-specific binding. Scatchard analysis revealed an apparent $K_D$ of approximately 14 and 12 nM respectively, with the number of apparent transferrin binding sites of $3 \times 10^5$ and $4 \times 10^5$ per cell.

To assess the biological effect of the HFE/TfR interaction, we characterized the transferrin-binding properties of the TfR in the presence or absence of HFE. For these studies we examined [$^{125}$I]-diferric transferrin binding to intact 293 cells engineered to over-express both $\beta_2$m and the wild-type or the Cys282Tyr mutant forms of HFE. The latter served as a baseline comparison since our earlier studies demonstrated that the Cys282Tyr mutant was not expressed on the cell surface (Feder, J. N., et al. *J. Biol. Chem.* 272:14025-14028 (1997)), and failed to interact with the TfR (FIGS. 1 and 2). In addition, the Cys282Tyr cell lines, like the wild-type cell lines, were selected for G418 resistance. The initial binding experiments were performed at 37° C., which allowed the total [$^{125}$I]-diferric transferrin bound to be representative of both surface-bound and internalized ligand (Karin, M. et al., *J. Biol. Chem.* 256:3245-3252 (1981); Octave, J. N. et al., *Eur. J. Biochem.* 123:235-240 (1982). The binding of [$^{125}$I]-diferric transferrin saturated at 150-300 nM on both Cys282Tyr mutant and wild-type HFE expressing cells (FIGS. 3A and B insets, which present data from two separate cell clones for each the wild-type and mutant HFE). When subjected to Scatchard analysis, the Cys282Tyr HFE mutant expressing clones bound transferrin with an apparent $K_D$ of approximately 12 and 14 nM and expressed approximately $3.0 \times 10^5$ and $4.0 \times 10^5$ transferrin binding sites per cell, respectively (FIG. 3A). The number of transferrin binding sites was calculated as follows. The X-intercept from the Scatchard plot gives the number of transferrin binding sites expressed in moles per liter (molarity). Multiplying by the volume of the assay (e.g. $7.5 \times 10^{-4}$ liters) yields the number of moles of transferrin binding sites. Dividing this number by the number of cells used in the assay yields the moles of binding sites per cell, which can be converted to number of transferrin binding sites per cell by multiplying by Avogadro's number.

Figure 3B:
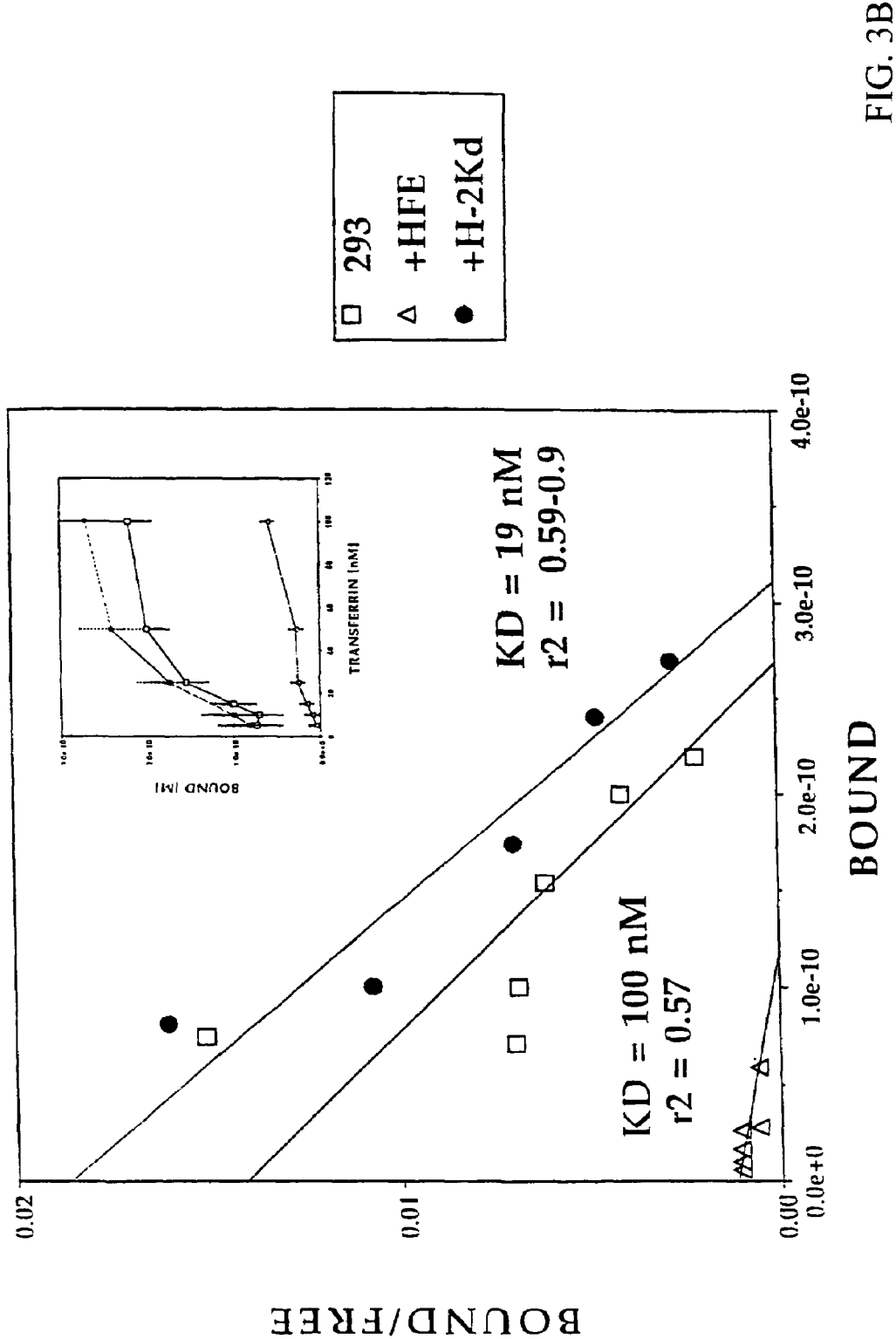
(FIG. 3B) Binding of $^{125}$I-transferrin to two clones of 293 cells overexpressing the wild type (surface) form of HFE (clone 7, open circles; clone 3, closed circles). Saturation of the transferrin receptors occurred at approximately the same concentration as in (FIG. 3A), however, the amount of transferrin bound was reduced 2-4 fold (inset). Scatchard analysis revealed that the $K_D$ for transferrin had been increased to 180 and 40 nM, and the number of apparent transferrin binding sites of 3.0×10⁵ and 4.0×10⁵ per cell.

These data were similar to values reported previously for other cultured cell lines (Mulford, C. A. et al. *J. Biol. Chem.* 263:5455-5461 (1988); Ward, J. H. et al. *J. Biol. Chem.* 257:10317-10323 (1982)), suggesting that binding and trafficking of the TfR to the cell surface in the mutant HFE-expressing cells was normal. By contrast, the affinity of the TfR for transferrin, in the wild-type HFE expressing clones, was reduced 4 and 15-fold to apparent $K_D$ values of 40 and 180 nM respectively, while expressing approximately $3.0 \times 10^5$ and $4 \times 10^5$ apparent transferrin binding sites per cell, respectively (FIG. 3B). Taken together, these results suggest that the presence or absence of the HFE protein on the cell surface affects the apparent $K_D$ of the TfR for transferrin.

Having previously shown that the His63Asp mutation had no effect on the binding of HFE to TfR, we next sought to determine if the mutation had an effect on the steady-state binding and uptake of transferrin to the transferrin receptor. Scatchard analysis on three clones overexpressing the His63Asp version of HFE on the cell surface all showed high affinity binding of transferrin ($K_D=12$ nM, FIG. 6A) to the TfR. This value is indistinguishable from that obtained with 293 cells clones 10 and 12 (expressing no surface HFE). However, the steady-state amount of transferrin bound in all three clones was reduced approximately 30% to that observed using 293 clones not expressing HFE (FIG. 6B). These data indicate that the His63Asp mutation has the functional consequence of eliminating the ability of HFE to abate the affinity of TfR for transferrin. As such, the His63Asp mutant acts as an antagonist of HFE action on TfR. Such result predicts higher cellular transferrin uptake; however, the amount of transferrin associated with the cell was still reduced. This function was apparently the result of the interaction that is maintained between the His63Asp mutant and TfR.

Figure 3C:
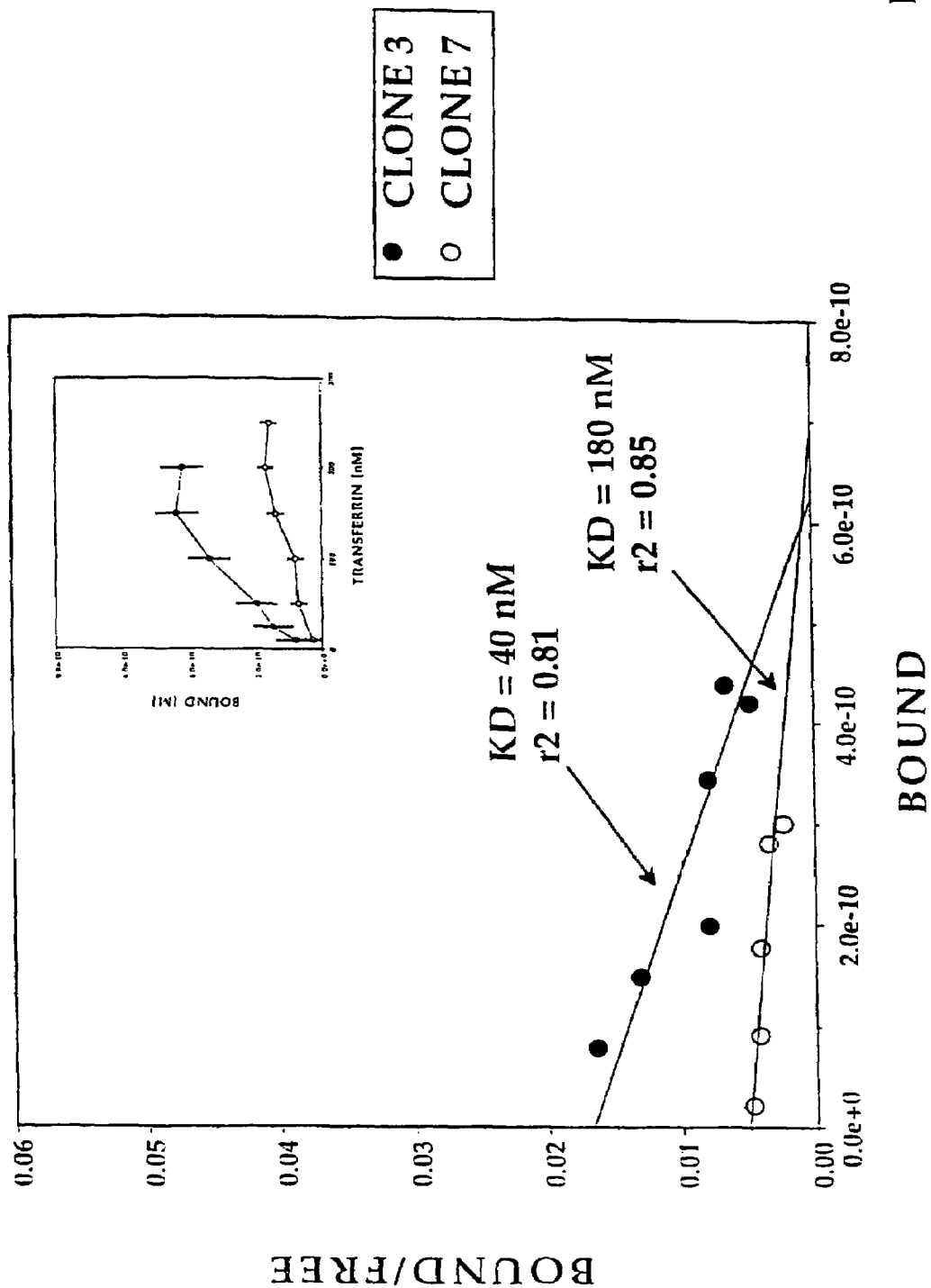
(FIG. 3C) Binding of [$^{125}$I]-transferrin to 293 cells in the presence of soluble HFE/$\beta_2$m heterodimers. 293 cells bind transferrin at 37° C., with an apparent $K_D$ of 19 nM (open squares), whereas in the presence of 2 µM of soluble HFE/$\beta_2$m heterodimers, the $K_D$ is increased 5 fold to 100 nM (open triangles). Control experiments using an identical amount of an MHC class I, H-2K$^d$ protein complexed with human $\beta_2$m failed to have any affect of transferrin binding (closed circles).
Figure 7:
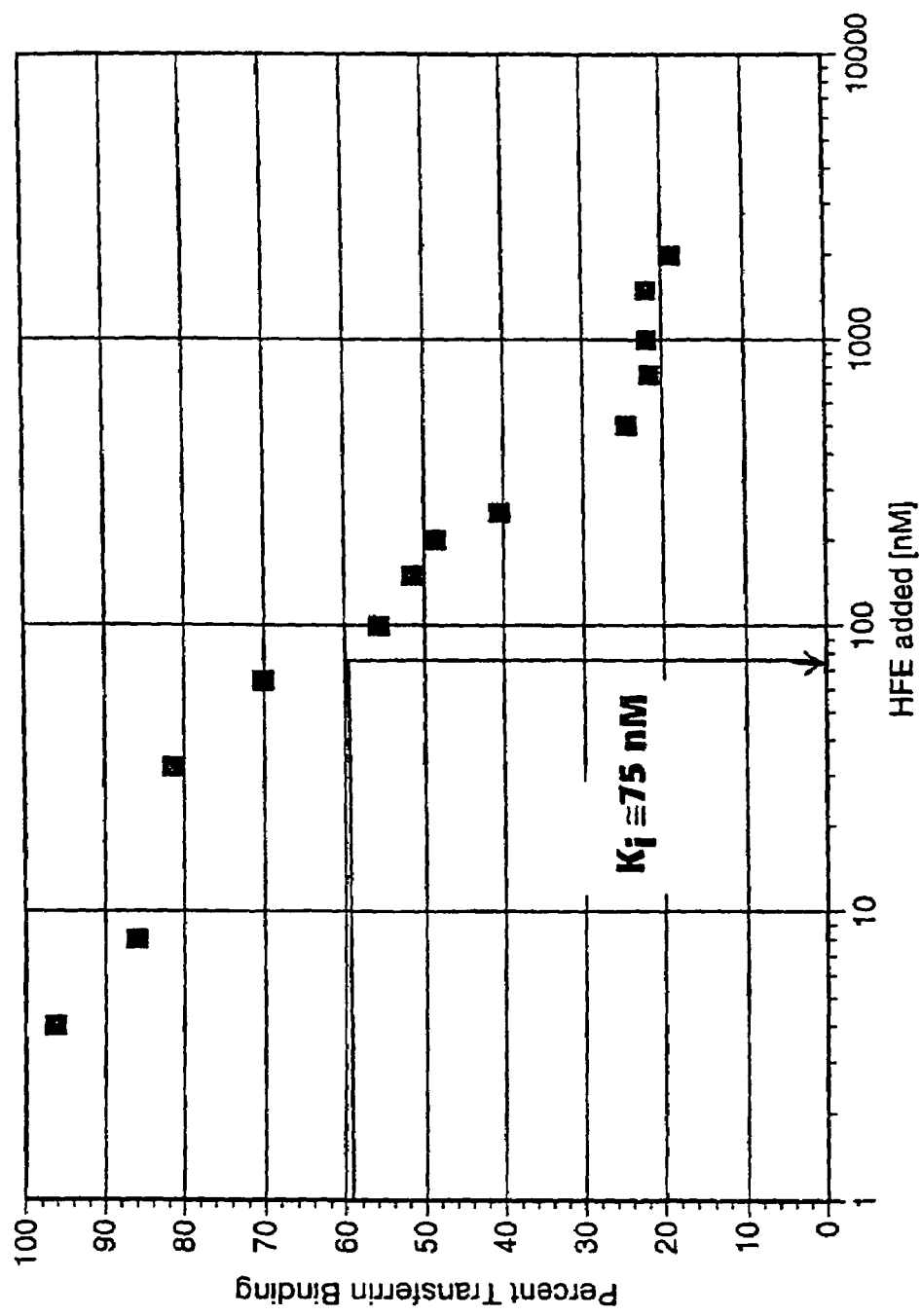
FIG. 7 depicts the inhibition of [$^{125}$I]-transferrin binding to the transferrin receptor by the addition of soluble HFE/$\beta_2$m heterodimers. The extent of change in the apparent $K_D$ was concentration-dependent from 30 nM to 750 nM soluble HFE/$\beta_2$m heterodimers, with an apparent $K_i$ of 75 nM.

As an alternative method to assess the effect of HFE on transferrin binding to the TfR, we added a soluble form of HFE/$\beta_2$m heterodimer to the culture medium of parental 293 cells. At 37° C. the binding of transferrin to parental 293 cells occurred with an apparent $K_D$ of 19 nM. In contrast, the apparent $K_D$ for the binding of transferrin to the TfR in the presence of 2 µM soluble HFE/$\beta_2$m heterodimer was increased 5-fold to 100 nM. The apparent number of transferrin binding sites was reduced from $1.25 \times 10^5$ to $5.0 \times 10^4$ per cell, a reduction of 60% (FIG. 3C), suggesting that the rate of receptor internalization without bound transferrin may be increased in the presence of HFE. The extent of change in the apparent $K_D$ was concentration-dependent from 30 nM to 750 nM soluble HFE/$\beta_2$m heterodimers, with an apparent $K_i$ of 75 nM (FIG. 7). In these experiments, transferrin binding assays were carried out as follows. Briefly, 293 cells were seeded at a density of $6 \times 10^5$ cell per well on fibronectin treated 6 well plates and grown overnight. The cells were washed once with DME, 1% FBS and then incubated with various concentrations of soluble HFE/$\beta_2$m heterodimers (2 nM to 2 µM) for 10 min at room temperature. [$^{125}$I]-transferrin was added to each well to a final concentration of 10 nM in a volume of 750 µl and incubated at 37° C. for 20 min. Untreated 293 cells were used to measure non-specific binding. The supernatants were removed and counted. The cells were then washed twice and lysed with 1% SDS and counted. These data demonstrated that the inhibition of transferrin binding is HFE dose dependent and predicts an estimated $K_i$ of 75 nM.

To determine whether the regulation of the apparent $K_D$ of the TfR was specific for the HFE protein, we added an equivalent amount of a soluble version of a classical MHC class I protein, purified H-2K$^d$ complexed with human $\beta_2$m (Fahnestock, M. L. et al., *Science* 258:1658-1662 (1992)) to the assay. Addition of this protein had no effect on transferrin binding to the TfR (FIG. 3C) demonstrating that the effect is not solely due to the presence of human $\beta_2$m alone. These experiments independently demonstrate that HFE can effectively lower the affinity of TfR for transferrin and that this effect appears to be a specific property of HFE.

The availability of soluble HFE/$\beta_2$m heterodimers permitted an investigation for other possible ligands for HFE, in particular small peptides which are known to bind class I molecules. The soluble HFE/$\beta_2$m heterodimers were expressed in CHO cells and analyzed for the presence of endogenous peptides by comparing amino acids recovered in acid eluates from HFE with those from other MHC-like proteins which either do or do not bind peptides (UL18 protein (Fahnestock, M. L., et al. *Immunity* 3:583-590 (1995)) and rat FcRn protein (Raghavah, M. et al., *Biochemistry* 32:8654-8660 (1993)), respectively). There was no evidence that peptides were bound to the HFE protein (Table 1). N-terminal protein sequencing demonstrated that no associating proteins were present with the exception of $\beta_2$m. Hence, our study has identified only one significant associated polypeptide, the transferrin receptor.

The primary defects in hereditary hemochromatosis appear to be increased iron absorption in the small intestine as well as increased iron deposition in major organs. We have demonstrated that HFE forms a stable complex with the transferrin receptor with the consequence of repressing transferrin uptake. The Cys282Tyr mutation is capable of eliminating this interaction. Without being limited to any one theory, these data suggest a mechanism for iron deposition in HFE where a loss of HFE transferrin uptake-repressor function would result in increased cellular uptake of iron. However, the role of this mechanism in intestinal iron absorption is less clear. Recent immunohistochemical studies have localized HFE to the intracellular portion of the cells in the deep crypts of the duodenum (Parkkila, S., et al. *Proc. Natl. Acad. Sci. USA* 94:2534-2539 (1997)), the same region where previous studies have localized the TfR (Banerjee, D. B. et al., *Gastroenterology* 91:861-869 (1986); Anderson, G. J. et al., *Gastroenterology* 98:576-585 (1990)). The role of the TfR in the cells of the deep crypts has long been thought to be limited to servicing the proliferative needs of these cells. In light of the association of HFE and the TfR, one must now reconsider the role of transferrin and its receptor in intestinal iron absorption. Regardless of the actual mechanism, the observations described here provide the first molecular link between HFE and iron metabolism.

Without being limited to any one theory, these data suggest the following model for how HFE regulates iron absorption. In normal individuals, the HFE/$\beta_2$m heterodimer binds the transferrin receptor. Upon binding the receptor either on the cell surface or during intracellular trafficking, the HFE/$\beta_2$m complex effects two separate regulatory aspects of receptor function. First, it lowers the receptor's ability to bind transferrin, i.e., the apparent affinity for transferrin is decreased as measured by a dissociation constant. Second, it alters the trafficking of the receptor by sequestration within the cell such that the receptor cannot be brought to the cell surface to bind transferrin or increases the rate in which the transferrin receptor is internalized without transferrin bound, or both. In either case, the effective number of transferrin receptors that can bind transferrin and bring iron into the cell is reduced.

The Cys282Tyr mutation reduces the ability of HFE protein to complex with the transferrin receptor. As a result, the individual absorbs greater amounts of iron because the transferrin receptor will bind transferrin at higher affinity, as shown experimentally herein by the lower dissociation constants observed in cells which express the Cys282Tyr mutant form of HFE. These cells will also show higher numbers of apparent transferrin binding sites because the ability to alter receptor trafficking is also missing. The long term result of this loss of regulation on transferrin uptake is iron-overload or hemochromatosis.

However, with the His63Asp mutation, only one of the two parts of the regulation is lost. His63Asp HFE allows the transferrin receptor to bind transferrin at high affinity, in a manner indistinguishable from when the HFE protein is not present at all. However, since His63Asp HFE is still able to complex with the receptor, it can still attenuate the amount of transferrin brought into the cell by lowering the apparent number of transferrin binding sites.

Our observations demonstrate that both forms of HFE regulation on the transferrin receptor can be achieved by exogenously adding soluble HFE/$\beta_2$m heterodimers to cells in culture. This regulation can be exploited as a therapy for diseases which involve the mis-regulation of the absorption of iron. For example, HFE/$\beta_2$m heterodimers or derivatives thereof could be used as an alternative to iron-chelators in the treatment of iron-overload syndromes of either primary or secondary nature. Furthermore, interfering with the HFE-transferrin receptor interaction can be exploited to increase iron uptake as a therapy for iron deficiency diseases.

II. Effects of Mutations in the TfR Receptor Gene

A. Frequency of a Novel Polymorphism

In this study the TfR gene was screened for possible polymorphisms associated with hemochromatosis. The cDNA sequence of human transferrin receptor (TFR) has been published by two groups with no amino acid polymorphism reported (McClelland et al., *Cell* 39:267-274 (1984), GenBank accession #M11507; Schneider et al., *Nature* 311:675-678 (1984), GenBank accession #X01060).

To discover amino acid polymorphisms in TfR genes we analyzed the DNA sequences of RT-PCR products from twenty three hereditary hemochromatosis patients and two unaffected individuals. This analysis revealed a novel DNA polymorphism in the cDNA sequence (A424G, with the first nucleotide in the initiator methionine codon designated as position 1) which caused a novel amino acid polymorphism (Ser142Gly). This A424G polymorphism was relatively common among hereditary hemochromatosis patients (Table 2), indicating involvement in the pathology of the disease.

TABLE 2

Frequency of the A424G polymorphism in the hereditary hemochromatosis patient chromosomes

| Genotype of HFE | A allele | G allele |
| --- | --- | --- |
| 24d1/24d1 homozygotes (patients) (n = 4) | 2 (50%) | 2 (50%) |
| 24d1/wild type heterozygotes (patients) (n = 4) | 0 (0%) | 4 (100%) |
| 24d1/24d2 heterozygotes (patients) (n = 6) | 3 (50%) | 3 (50%) |
| 24d2/wild type heterozygotes (patients) (n = 14) | 8 (57%) | 6 (43%) |
| wild type/wild type homozygotes (patients) (n = 18) | 8 (44%) | 10 (56%) |
| wild type/wild type homozygotes (unaffected) (n = 4) | 3 (75%) | 1 (25%) |

B. Screening for A424G

One of the methods which can be used to detect this polymorphism is oligonucleotide ligation assay (OLA). (Delahunty et al., *Am. J. Hum. Genet.* 58:1239-1246 (1996)). The first step of this assay is amplification of the DNA fragment containing the polymorphism by polymerase chain reaction (PCR). This can be achieved by using genomic DNA as a starting material. Another material which can be used as a starting material for PCR is "first strand cDNA". "First strand cDNA" can be synthesized from poly (A) RNA using reverse transcriptase; this method is well known in the art (e.g., Sambrook et al. *Molecular Cloning: A Laboratory Manual* (Cold Spring Harbor Laboratory, Cold Spring Harbor, N.Y. (1989)).

For PCR amplification from first strand cDNA, one can design PCR primers based on the available TFR cDNA sequence. Oligonucleotides needed for OLA can also be designed based on the cDNA sequence. One example of such a set of oligonucleotides is:

```
TRFd1.P3 (PCR forward primer):
AGAAAGTTGTCGGAGAAACTGG.               (SEQ ID NO:9)

TFRd1.P4 (PCR reverse primer):
ACGAGGGACATATGAATTTTCA.               (SEQ ID NO:10)

TFRd1.A (5' side OLA oligonucleotide for 424A
allele):
biotin-GGACAGCACAGACTTCACCA.          (SEQ ID NO:11)
```

-continued

```
TFRd1.G (5' side OLA oligonucleotide for 424G
allele):
biotin-GGACAGCACAGACTTCACCG.          (SEQ ID NO:12)

TFRd1.X (3' side common OLA oligonucleotide):
GCACCATCAAGCTGCTGAAT-digoxygenin.     (SEQ ID NO:13)
```

All references (including books, articles, papers, patents, and patent applications) cited herein are hereby expressly incorporated by reference in their entirety for all purposes.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

We claim:

1. A method of treating hereditary hemochromatosis in a patient with a hereditary hemochromatosis ("HFE") gene mutation comprising administering to a patient a therapeutically effective amount of a soluble HFE polypeptide comprising SEQ ID NO: 8, wherein the soluble HFE polypeptide is complexed to β-2-microglobulin.

* * * * *

SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
       (A) LENGTH: 2739 base pairs
       (B) TYPE: nucleic acid
       (C) STRANDEDNESS: single
       (D) TOPOLOGY: linear (xi) SEQUENCE DESCRIPTION: SEQ ID NO: 1:

```
CCACGCGTCC GGGGGACAC  TGGATCACCT AGTGTTTCAC AAGCAGGTAC CTTCTGCTGT      60

AGGAGAGAGA GAACTAAAGT TCTGAAAGAC CTGTTGCTTT TCACCAGGAA GTTTTACTGG     120

GCATCTCCTG AGCCTAGGCA ATAGCTGTAG GGTGACTTCT GGAGCCATCC CCGTTTCCCC     180

GCCCCCCAAA AGAAGCGGAG ATTTAACGGG GACGTGCGGC CAGAGCTGGG GAAATGGGCC     240

CGCGAGCCAG GCCGGCGCTT CTCCTCCTGA TGCTTTTGCA GACCGCGGTC CTGCAGGGGC     300

GCTTGCTGCG TTCACACTCT CTGCACTACC TCTTCATGGG TGCCTCAGAG CAGGACCTTG     360

GTCTTTCCTT GTTTGAAGCT TTGGGCTACG TGGATGACCA GCTGTTCGTG TTCTATGATC     420

ATGAGAGTCG CCGTGTGGAG CCCCGAACTC CATGGGTTTC CAGTAGAATT TCAAGCCAGA     480

TGTGGCTGCA GCTGAGTCAG AGTCTGAAAG GGTGGGATCA CATGTTCACT GTTGACTTCT     540

GGACTATTAT GGAAAATCAC AACCACAGCA AGGAGTCCCA CACCCTGCAG GTCATCCTGG     600

GCTGTGAAAT GCAAGAAGAC AACAGTACCG AGGGCTACTG GAAGTACGGG TATGATGGGC     660

AGGACCACCT TGAATTCTGC CCTGACACAC TGGATTGGAG AGCAGCAGAA CCCAGGGCCT     720

GGCCCACCAA GCTGGAGTGG GAAAGGCACA AGATTCGGGC CAGGCAGAAC AGGGCCTACC     780

TGGAGAGGGA CTGCCCTGCA CAGCTGCAGC AGTTGCTGGA GCTGGGGAGA GGTGTTTTGG     840

ACCAACAAGT GCCTCCTTTG GTGAAGGTGA CACATCATGT GACCTCTTCA GTGACCACTC     900
```

```
TACGGTGTCG GGCCTTGAAC TACTACCCCC AGAACATCAC CATGAAGTGG CTGAAGGATA    960

AGCAGCCAAT GGATGCCAAG GAGTTCGAAC CTAAAGACGT ATTGCCCAAT GGGGATGGGA   1020

CCTACCAGGG CTGGATAACC TTGGCTGTAC CCCCTGGGGA AGAGCAGAGA TATACGTGCC   1080

AGGTGGAGCA CCCAGGCCTG GATCAGCCCC TCATTGTGAT CTGGGAGCCC TCACCGTCTG   1140

GCACCCTAGT CATTGGAGTC ATCAGTGGAA TTGCTGTTTT TGTCGTCATC TTGTTCATTG   1200

GAATTTGTT CATAATATTA AGGAAGAGGC AGGGTTCAAG AGGAGCCATG GGCACTACG    1260

TCTTAGCTGA ACGTGAGTGA CACGCAGCCT GCAGACTCAC TGTGGGAAGG AGACAAAACT   1320

AGAGACTCAA AGAGGGAGTG CATTTATGAG CTCTTCATGT TTCAGGAGAG AGTTGAACCT   1380

AAACATAGAA ATTGCCTGAC GAACTCCTTG ATTTTAGCCT TCTCTGTTCA TTTCCTCAAA   1440

AAGATTTCCC CATTTAGGTT TCTGAGTTCC TGCATGCCGG TGATCCCTAG CTGTGACCTC   1500

TCCCCTGGAA CTGTCTCTCA TGAACCTCAA GCTGCATCTA GAGGCTTCCT TCATTTCCTC   1560

CGTCACCTCA GAGACATACA CCTATGTCAT TCATTTCCT ATTTTGGAA GAGGACTCCT    1620

TAAATTTGGG GGACTTACAT GATTCATTTT AACATCTGAG AAAAGCTTTG AACCCTGGGA   1680

CGTGGCTAGT CATAACCTTA CCAGATTTTT ACACATGTAT CTATGCATTT CTGGACCCG    1740

TTCAACTTTT CCTTTGAATC CTCTCTCTGT GTTACCCAGT AACTCATCTG TCACCAAGCC   1800

TTGGGGATTC TTCCATCTGA TTGTGATGTG AGTTGCACAG CTATGAAGGC TGTGCACTGC   1860

ACGAATGGAA GAGGCACCTG TCCCAGAAAA AGCATCATGG CTATCTGTGG GTAGTATGAT   1920

GGGTGTTTTT AGCAGGTAGG AGGCAAATAT CTTGAAAGGG GTTGTGAAGA GGTGTTTTTT   1980

CTAATTGGCA TGAAGGTGTC ATACAGATTT GCAAAGTTTA ATGGTGCCTT CATTTGGGAT   2040

GCTACTCTAG TATTCCAGAC CTGAAGAATC ACAATAATTT TCTACCTGGT CTCTCCTTGT   2100

TCTGATAATG AAAATTATGA TAAGGATGAT AAAAGCACTT ACTTCGTGTC CGACTCTTCT   2160

GAGCACCTAC TTCATGCAT TACTGCATGC ACTTCTTACA ATAATTCTAT GAGATAGGTA    2220

CTATTATCCC CATTTCTTTT TTAAATGAAG AAAGTGAAGT AGGCCGGGCA CGGTGGCTCG   2280

CGCCTGTGGT CCCAGGGTGC TGAGATTGCA GGTGTGAGCC ACCCTGCCCA GCCGTCAAAA   2340

GAGTCTTAAT ATATATATCC AGATGGCATG TGTTTACTTT ATGTTACTAC ATGCACTTGG   2400

CTGCATAAAT GTGGTACAAC CATTCTGTCT TGAAGGGCAG GTGCTTCAGG ATACCATATA   2460

CAGCTCAGAA GTTTCTTCTT TAGGCATTAA ATTTTAGCAA AGATATCTCA TCTCTTCTTT   2520

TAAACCATTT TCTTTTTTTG TGGTTAGAAA AGTTATGTAG AAAAAAGTAA ATGTGATTTA   2580

CGCTCATTGT AGAAAAGCTA TAAAATGAAT ACAATTAAAG CTGTTATTTA ATTAGCCAGT   2640

GAAAAACTAT TAACAACTTG TCTATTACCT GTTAGTATTA TTGTTGCATT AAAAATGCAT   2700

ATACTTTAAT AAATGTACAT TGTATTGTAA AAAAAAAA                           2739
```

(2) INFORMATION FOR SEQ ID NO: 2:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 2:

```
Met Gly Pro Arg Ala Arg Pro Ala Leu Leu Leu Leu Met Leu Leu Gln
 1               5                  10                  15

Thr Ala Val Leu Gln Gly
```

(2) INFORMATION FOR SEQ ID NO: 3:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 3:

```
Arg Leu Leu Arg Ser His Ser Leu His Tyr Leu Phe Met Gly Ala Ser
 1               5                  10                  15

Glu Gln Asp Leu Gly Leu Ser Leu Phe Glu Ala Leu Gly Tyr Val Asp
            20                  25                  30

Asp Gln Leu Phe Val Phe Tyr Asp His Glu Ser Arg Arg Val Glu Pro
        35                  40                  45

Arg Thr Pro Trp Val Ser Ser Arg Ile Ser Ser Gln Met Trp Leu Gln
    50                  55                  60

Leu Ser Gln Ser Leu Lys Gly Trp Asp His Met Phe Thr Val Asp Phe
65                  70                  75                  80

Trp Thr Ile Met Glu Asn His Asn His Ser Lys Glu
                85                  90
```

(2) INFORMATION FOR SEQ ID NO: 4:

(i) SEQUENCE CHARACTERISTICS:
        (A) LENGTH: 91 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 4:

```
Ser His Thr Leu Gln Val Ile Leu Gly Cys Glu Met Gln Glu Asp Asn
 1               5                  10                  15

Ser Thr Glu Gly Tyr Trp Lys Tyr Gly Tyr Asp Gly Gln Asp His Leu
            20                  25                  30

Glu Phe Cys Pro Asp Thr Leu Asp Trp Arg Ala Ala Glu Pro Arg Ala
        35                  40                  45

Trp Pro Thr Lys Leu Glu Trp Glu Arg His Lys Ile Arg Ala Arg Gln
    50                  55                  60

Asn Arg Ala Tyr Leu Glu Arg Asp Cys Pro Ala Gln Leu Gln Gln Leu
65                  70                  75                  80

Leu Glu Leu Gly Arg Gly Val Leu Asp Gln Gln
                85                  90
```

(2) INFORMATION FOR SEQ ID NO: 5:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 5:

```
Val Pro Pro Leu Val Lys Val Thr His His Val Thr Ser Ser Val Thr
 1               5                  10                  15
```

```
Thr Leu Arg Cys Arg Ala Leu Asn Tyr Tyr Pro Gln Asn Ile Thr Met
            20                  25                  30

Lys Trp Leu Lys Asp Lys Gln Pro Met Asp Ala Lys Glu Phe Glu Pro
            35                  40                  45

Lys Asp Val Leu Pro Asn Gly Asp Gly Thr Tyr Gln Gly Trp Ile Thr
            50                  55                  60

Leu Ala Val Pro Pro Gly Glu Glu Gln Arg Tyr Thr Cys Gln Val Glu
 65                  70                  75                  80

His Pro Gly Leu Asp Gln Pro Leu Ile Val Ile Trp
                85                  90
```

(2) INFORMATION FOR SEQ ID NO: 6:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 6:

```
Glu Pro Ser Pro Ser Gly Thr Leu Val Ile Gly Val Ile Ser Gly Ile
 1               5                  10                  15

Ala Val Phe Val Val Ile Leu Phe Ile Gly Ile Leu Phe Ile Ile Leu
            20                  25                  30
```

(2) INFORMATION FOR SEQ ID NO: 7:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO: 7:

```
Arg Lys Arg Gln Gly Ser Arg Gly Ala Met Gly His Tyr Val Leu Ala
 1               5                  10                  15

Glu Arg Glu
```

(2) INFORMATION FOR SEQ ID NO: 8:

(i) SEQUENCE CHARACTERISTICS:
        (A) LENGTH: 276 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 8:

```
Arg Leu Leu Arg Ser His Ser Leu His Tyr Leu Phe Met Gly Ala Ser
 1               5                  10                  15

Glu Gln Asp Leu Gly Leu Ser Leu Phe Glu Ala Leu Gly Tyr Val Asp
            20                  25                  30

Asp Gln Leu Phe Val Phe Tyr Asp His Glu Ser Arg Arg Val Glu Pro
            35                  40                  45

Arg Thr Pro Trp Val Ser Ser Arg Ile Ser Ser Gln Met Trp Leu Gln
            50                  55                  60

Leu Ser Gln Ser Leu Lys Gly Trp Asp His Met Phe Thr Val Asp Phe
```

```
        65                  70                  75                  80
Trp Thr Ile Met Glu Asn His Asn His Ser Lys Glu Ser His Thr Leu
                85                  90                  95

Gln Val Ile Leu Gly Cys Glu Met Gln Glu Asp Asn Ser Thr Glu Gly
            100                 105                 110

Tyr Trp Lys Tyr Gly Tyr Asp Gly Gln Asp His Leu Glu Phe Cys Pro
        115                 120                 125

Asp Thr Leu Asp Trp Arg Ala Ala Glu Pro Arg Ala Trp Pro Thr Lys
    130                 135                 140

Leu Glu Trp Glu Arg His Lys Ile Arg Ala Arg Gln Asn Arg Ala Tyr
145                 150                 155                 160

Leu Glu Arg Asp Cys Pro Ala Gln Leu Gln Gln Leu Leu Glu Leu Gly
                165                 170                 175

Arg Gly Val Leu Asp Gln Gln Val Pro Pro Leu Val Lys Val Thr His
            180                 185                 190

His Val Thr Ser Ser Val Thr Thr Leu Arg Cys Arg Ala Leu Asn Tyr
        195                 200                 205

Tyr Pro Gln Asn Ile Thr Met Lys Trp Leu Lys Asp Lys Gln Pro Met
    210                 215                 220

Asp Ala Lys Glu Phe Glu Pro Lys Asp Val Leu Pro Asn Gly Asp Gly
225                 230                 235                 240

Thr Tyr Gln Gly Trp Ile Thr Leu Ala Val Pro Pro Gly Glu Glu Gln
                245                 250                 255

Arg Tyr Thr Cys Gln Val Glu His Pro Gly Leu Asp Gln Pro Leu Ile
            260                 265                 270

Val Ile Trp Glu
        275

(2) INFORMATION FOR SEQ ID NO: 9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 9:

AGAAAGTTGT CGGAGAAACT GG                                            22

(2) INFORMATION FOR SEQ ID NO: 10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO: 10:

ACGAGGGACA TATGAATTTT CA                                            22

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 11:

GGACAGCACA GACTTCACCA                                               20
```

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

GGACAGCACA GACTTCACCG                    20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 13:

GCACCATCAA GCTGCTGAAT                    20